US011801218B2

(12) United States Patent
Croyle et al.

(10) Patent No.: US 11,801,218 B2
(45) Date of Patent: *Oct. 31, 2023

(54) METHODS FOR INDUCING AN IMMUNE RESPONSE VIA BUCCAL AND/OR SUBLINGUAL ADMINISTRATION OF A VACCINE

(71) Applicant: BOARD OF REGENTS, THE UNIVERSITY OF TEXAS SYSTEM, Austin, TX (US)

(72) Inventors: Maria A. Croyle, Austin, TX (US); Jin Huk Choi, Austin, TX (US); Stephen Clay Schafer, Austin, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 7 days.

This patent is subject to a terminal disclaimer.

(21) Appl. No.: 17/502,785

(22) Filed: Oct. 15, 2021

(65) Prior Publication Data
US 2022/0096368 A1 Mar. 31, 2022

Related U.S. Application Data

(60) Continuation of application No. 16/845,930, filed on Apr. 10, 2020, now abandoned, which is a division of application No. 15/591,725, filed on May 10, 2017, now Pat. No. 10,646,438, which is a division of application No. 13/750,774, filed on Jan. 25, 2013, now Pat. No. 9,675,550, which is a continuation-in-part of application No. PCT/US2011/045379, filed on Jul. 26, 2011.

(60) Provisional application No. 61/367,631, filed on Jul. 26, 2010.

(51) Int. Cl.
| | | |
|---|---|---|
| A61K 9/00 | (2006.01) |
| A61K 39/12 | (2006.01) |
| C12N 1/04 | (2006.01) |
| C12N 7/00 | (2006.01) |
| A61K 47/26 | (2006.01) |
| A61K 39/00 | (2006.01) |

(52) U.S. Cl.
CPC ............ *A61K 9/006* (2013.01); *A61K 39/12* (2013.01); *A61K 47/26* (2013.01); *C12N 1/04* (2013.01); *C12N 7/00* (2013.01); *A61K 2039/5256* (2013.01); *A61K 2039/541* (2013.01); *C12N 2710/10343* (2013.01); *C12N 2710/10351* (2013.01); *C12N 2760/14134* (2013.01)

(58) Field of Classification Search
None
See application file for complete search history.

(56) References Cited

U.S. PATENT DOCUMENTS

| | | |
|---|---|---|
| 2,595,793 A | 5/1952 | Kay |
| 3,527,646 A | 9/1970 | Scheick et al. |
| 4,251,509 A | 2/1981 | Hanson et al. |
| 5,569,468 A | 10/1996 | Modi |
| 5,595,760 A | 1/1997 | Cherif-Cheikh |
| 6,552,024 B1 | 4/2003 | Chen et al. |
| 9,974,850 B2 * | 5/2018 | Croyle ............... A61K 39/12 |
| 10,279,029 B2 * | 5/2019 | Croyle ............... A61K 39/12 |
| 10,646,438 B2 * | 5/2020 | Croyle ............... A61K 47/26 |
| 2002/0099001 A1 | 7/2002 | Habberfield |
| 2004/0036193 A1 | 2/2004 | Berry et al. |
| 2007/0059807 A1 | 3/2007 | Wisniewski et al. |
| 2007/0104734 A1 | 5/2007 | Oomens et al. |
| 2009/0092666 A1 | 4/2009 | Brown et al. |
| 2009/0155351 A1 | 6/2009 | Hejl et al. |
| 2010/0209359 A1 | 8/2010 | Foster |
| 2011/0059919 A1 | 3/2011 | Grassauer et al. |
| 2011/0305768 A1 | 12/2011 | Mao et al. |
| 2013/0259945 A1 | 10/2013 | Powell |
| 2014/0120139 A1 | 5/2014 | Croyle et al. |
| 2015/0125495 A1 | 5/2015 | Wood et al. |
| 2016/0296616 A1 | 10/2016 | Croyle et al. |
| 2019/0298836 A1 * | 10/2019 | Croyle ............... A61K 9/0019 |
| 2020/0353068 A1 * | 11/2020 | Croyle ............... A61K 39/39 |

FOREIGN PATENT DOCUMENTS

| | | |
|---|---|---|
| CA | 2853894 | 5/2013 |
| WO | WO 02/101412 | 12/2002 |
| WO | WO 2012/018628 | 2/2012 |
| WO | WO 2008/143782 | 5/2018 |
| WO | WO 2018-085495 | 5/2018 |

OTHER PUBLICATIONS

Anatrace™ Specialty Detergents Products P5016-PMAL-C16 (poly (Maleic Anhydride-Alt-1-Octadecene) substituted with 3-(Dimethylamino) Propylamine from https://www.anatrace.com/Products/Specialty-Detergents-Products/AMPHIPOL/P5016, accessed Jul. 22, 2017.

Appledorn, Daniel M., et al. "Sublingual administration of an adenovirus serotvpe 5 (Ad5)-based vaccine confirms Toll-like receptor agonist activity in the oral cavity and elicits improved mucosal and systemic cell-mediated responses against HIV antigens despite preexisting Ad5 immunity." *Clin. Vaccine Immunol.* 18.1 (2011): 150-160.

Di Corato et al., "Water solubilization of hydrophobic nanocrystals by means of poly(maleic anhydride-alt-1-octadecene)," *J. Mater. Chem.*, 18:1991-1996, 2008.

Gorzelle et al., "Amphipols can support the activity of a membrane enzyme," *J. Am. Chem. Soc.*, 124:11594-11595, 2002.

(Continued)

*Primary Examiner* — Shanon A. Foley
*Assistant Examiner* — Myron G Hill
(74) *Attorney, Agent, or Firm* — Parker Highlander PLLC

(57) ABSTRACT

Vaccine compositions that may be administered to a subject via the buccal and/or sublingual mucosa are provided. Methods for administration and preparation of such vaccine compositions are also provided.

20 Claims, 21 Drawing Sheets
(3 of 21 Drawing Sheet(s) Filed in Color)

(56) References Cited

OTHER PUBLICATIONS

Jonsson-Schmunk and Croyle, "A long-lasting, single dose nasal vaccine for Ebola: a practical armament for an outbreak with significant global impact", *Expert Rev. Anti. Infect. Ther.*, 13(5): 527-530, 2015.

Kerwin, Bruce A. "Polysorbates 20 and 80 used in the formulation of protein biotherapeutics: structure and degradation pathways." *Journal of Pharmaceutical Sciences* 97.8 (2008): 2924-2935.
Popot et al., "Amphipols from A to Z," *Ann. Rev. Biophys.*, 40:379-408, 2011.
Rehermann et al., "The cytotoxic T lymphocyte response to multiple hepatitis B virus polymerase epitopes during and after acute viral hepatitis," *J. Exp. Med.*, 181:1047-1058, 1995.
Sigma-Aldrich, "Detergent Properties and Applications," retrieved from <URL=https://web.archive.org/web/20160222144312/https://www,sigmaaldrich.com/technical-documents/articles/biofiles/detergent-properties.html> on Mar. 22, 2018, published online on Feb. 22, 2016.
Voros et al., "Immunogenic compositions and uses thereof," *J. Virol.*, 88(5):2584-2594, 2014.
Wikipedia, "Immunogenicity," retrieved from <URL=https://en.wikipedia.org/w/index.php?title=Immunogenicity&oldid=710810712> on Mar. 22, 2018, published online on Mar. 19, 2016.
Wikipedia, "Receptor (biochemistry)," retrieved from <URL=https://en.wikipedia.org/w/index.php?title=Receptor_(biochemistry)&oldid=723830874> on Mar. 23, 2018, published online on Jun. 5, 2016.

* cited by examiner

METHODS FOR INDUCING AN IMMUNE RESPONSE VIA BUCCAL AND/OR SUBLINGUAL ADMINISTRATION OF A VACCINE

CROSS-REFERENCE TO RELATED APPLICATIONS

This application is a continuation of U.S. application Ser. No. 16/845,930, filed Apr. 10, 2020, which is a divisional of U.S. application Ser. No. 15/591,725, filed May 10, 2017, now U.S. Pat. No. 10,646,438, which is a divisional of U.S. application Ser. No. 13/750,774, filed Jan. 25, 2013, now U.S. Pat. No. 9,675,550, which is a continuation-in-part of International Application No. PCT/US11/45379, filed Jul. 26, 2011, which claims the benefit of U.S. Provisional Application No. 61/367,631, filed Jul. 26, 2010, the entire disclosures of each of which are hereby incorporated by reference.

STATEMENT OF GOVERNMENT INTEREST

This invention was made with government support under Grant Number U01 AI078045 awarded by the National Institutes of Health. The government has certain rights in the invention.

BACKGROUND

Vaccination has increased the average human lifespan worldwide more than 10 years during the 20th century. Breakthroughs in immunology, molecular biology and biochemistry in the last 25 years produced more than half of the vaccines used during the last 100 years. Despite this, little progress has been made in delivery since most are injectable and require strict maintenance of cold chain conditions.

Injectable vaccines have various drawbacks. Injections are the most common reason for iatrogenic pain in childhood and deter many from immunization. Injectable vaccines pose a significant risk to the safety of medical staff, patients and community. And most vaccines are unstable at ambient temperatures and require refrigeration.

SUMMARY

The present disclosure generally relates to vaccine compositions that may be administered to a subject via the buccal and/or sublingual mucosa. In some embodiments, the present disclosure also relates to methods for administration and preparation of such vaccine compositions.

In one embodiment, the present disclosure provides a composition comprising an antigen dispersed within an amorphous solid.

In another embodiment, the present disclosure provides a method comprising administering a vaccine composition comprising an antigen dispersed within an amorphous solid to the buccal and/or sublingual mucosa of a subject in an amount effective to induce an immune response to the antigen.

In yet another embodiment, the present disclosure provides a method comprising providing an antigen and a solution comprising a sugar, sugar derivative or a combination thereof; dispersing the antigen within the solution to form a mixture; and allowing the mixture to harden so as to form an amorphous solid.

The features and advantages of the present invention will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings. The patent or application file contains at least one drawing executed in color. Copies of this patent or patent application publication with color drawing(s) will be provided by the Office upon request and payment of the necessary fee.

Figure 16A:
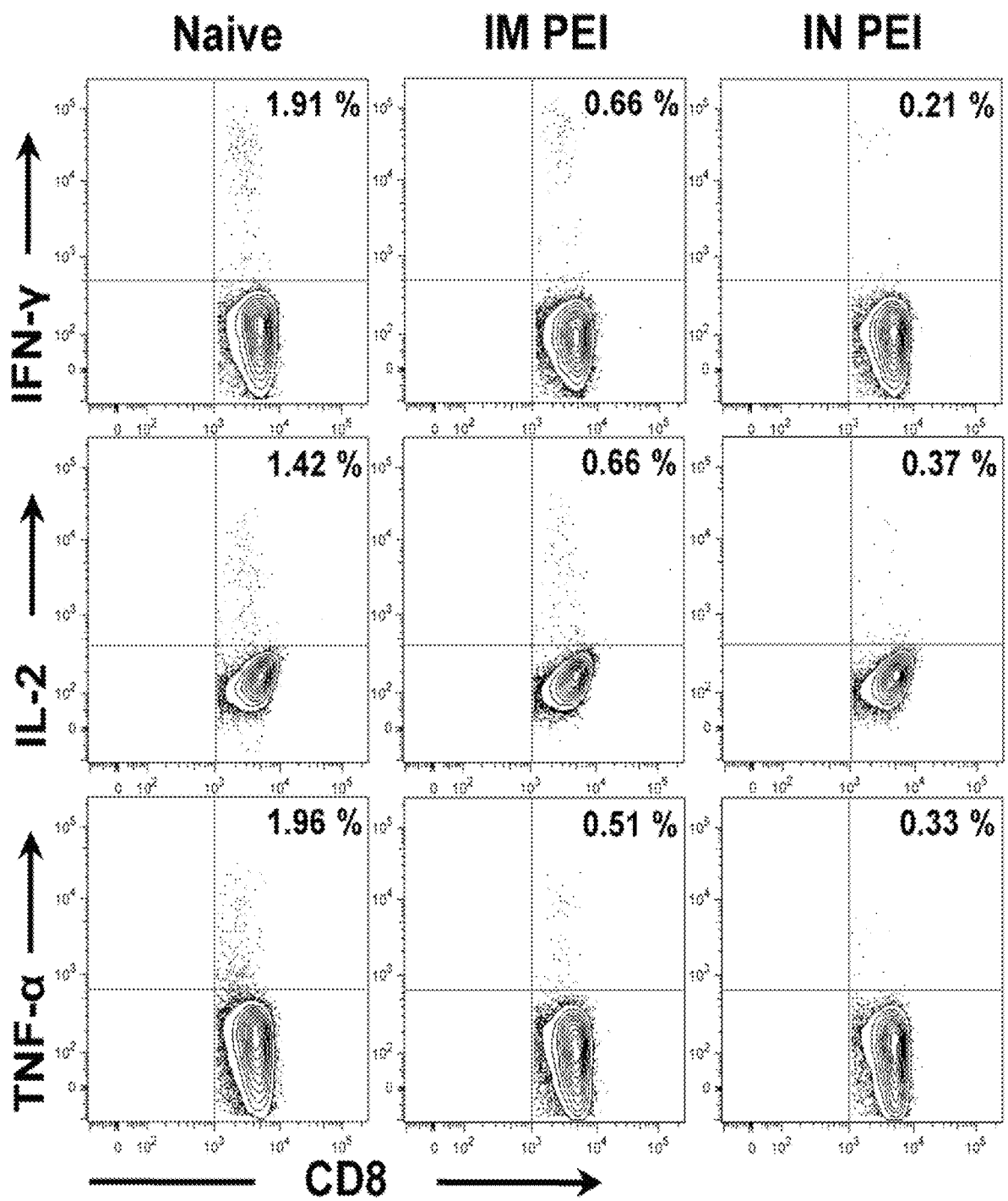
Figure 16B:
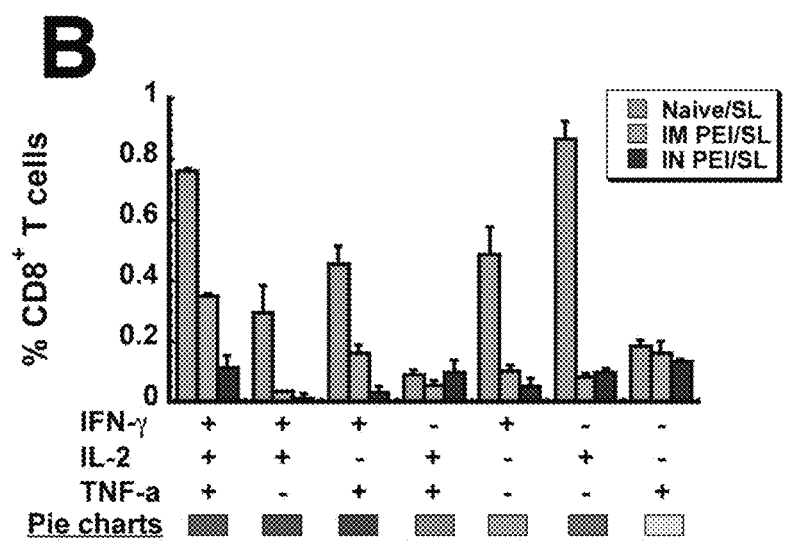
Figure 16C:
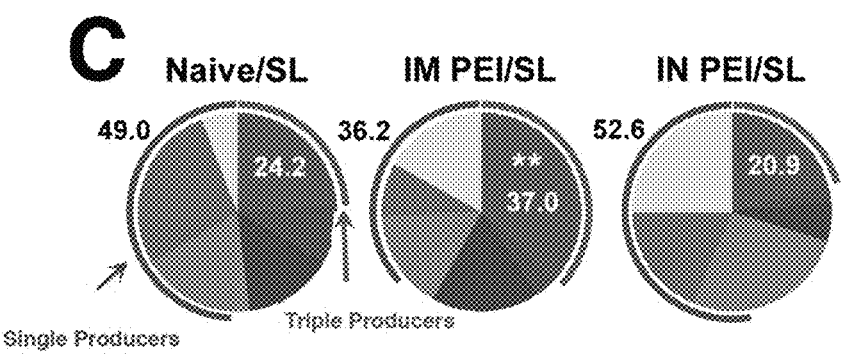

FIGS. 16A-16C show that pre-existing immunity (PEI) to the adenovirus vaccine carrier boosts the antigen-specific immune response induced by sublingual immunization. (A) shows analysis of CD8+ T cells expressing immunoreactive cytokines by flow cytometery (FACS). Numbers written in the upper right corner of each scatter plot represent the portion of each cell population that was activated by Ebola Zaire GP-specific peptide sequences. (B) shows cumulate analysis of FACS data. Each positively responding cell is assigned to total 7 possible combinations of IFN-γ, IL-2 and TNF-α and final numbers presented as a bar graph. (C) depicts Zaire GP-specific multifunctional CD8$^+$ T cells in pie chart format. Triple producers are depicted in the red arc. The blue arc highlights cells producing IFN-γ only. Numbers in the pie chart denote the percentage of triple producers in a given population. Results are reported as the mean± the standard error of the mean. **p<0.01, one-way ANOVA, Bonferroni/Dunn post-hoc analysis.

FIGS. 17A-17D show that pre-existing immunity (PEI) to the adenovirus vaccine carrier improves survival after lethal challenge following sublingual immunization. Naive mice and those with prior exposure to adenovirus serotype 5 by IM or IN administration (indicated by IM PEI or IN PEI, respectively, n=10) were challenged with a lethal dose of MA-ZEBOV (30,000×LD$_{50}$) by I.P. injection 28 days after SL immunization. (A) Kaplan-Meier survival curve; (B) Body weight profile after challenge; (C) Serum alanine (ALT) and aspartate (AST) aminotransferase levels; (D) Serum cytokines post-challenge. For (C) & (D), all samples were taken 14 days post challenge from survivors. Samples from non-survivors were taken at time of death. * indicates a significant difference with respect to the Naive/SL treatment group. *p<0.05, one-way ANOVA, Bonferroni/Dunn post-hoc analysis.

Figure 18A:
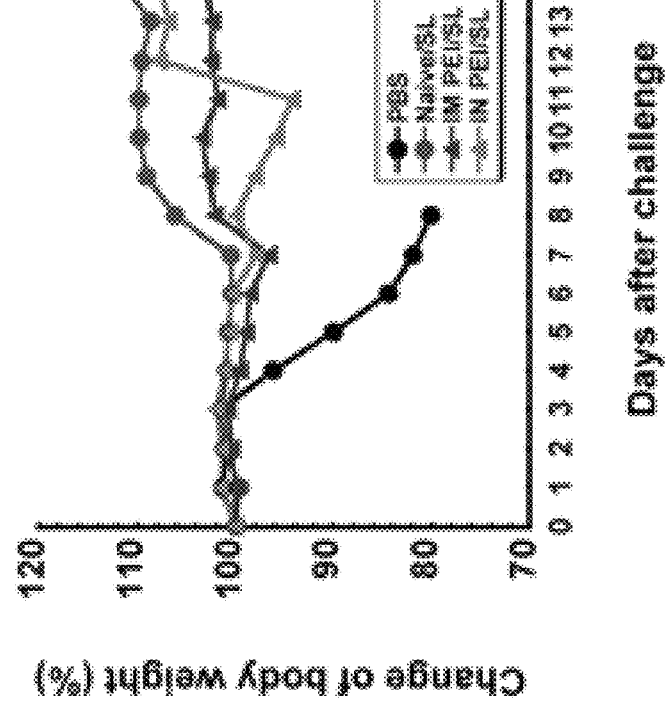
Figure 18B:
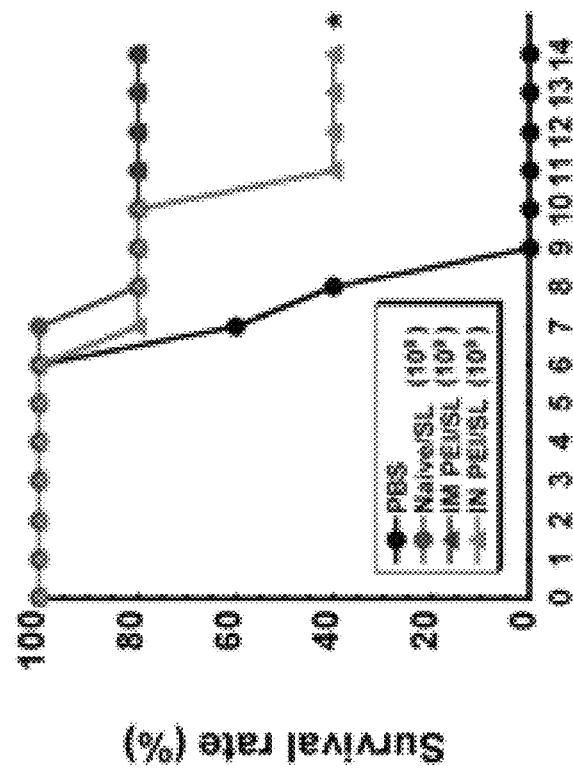
Figure 18C:
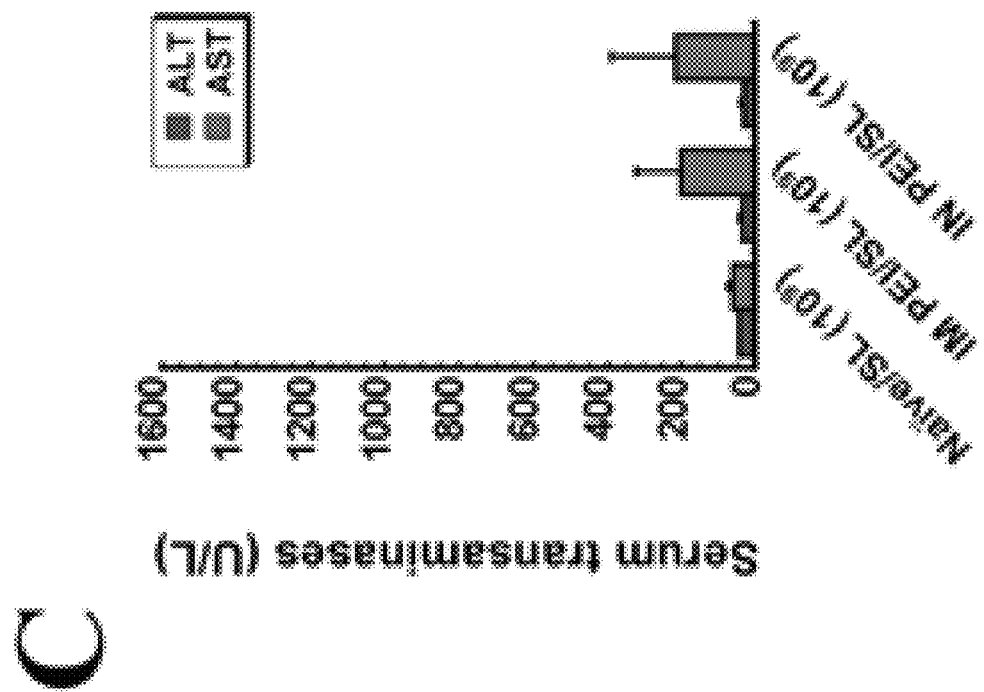

FIGS. 18A-18C shows results following sublingual immunization in Guinea Pigs. Naive guinea pigs and those with prior exposure to Ad5 by the IM or IN routes (indicated by IM or IN PEI, respectively, n=5) were challenged with a lethal dose of guinea pig-adapted Zaire Ebola virus (1,000× LD$_{50}$). (A) Kaplan-Meier survival curve. (B) Body weight profile after challenge. (C) Serum alanine (ALT) and aspartate (AST) aminotransferase levels post-challenge. For (C), samples from non-survivors were taken at time of death. Samples from survivors were taken 14 days post-challenge. * indicates a significant difference with respect to the Naive/SL treatment group. *, p<0.05, one-way ANOVA, Bonferroni/Dunn post-hoc analysis.

FIGS. 19A-19D show that formulations of the present disclosure can reconstitute the antigen-specific polyfunctional T cell and Memory Response in mice. Panels A-C show effector CD8 T cell responses. Ten days after vaccination, mononuclear cells from various tissues were harvested, pooled according to treatment, stimulated with an Ebola Zaire GP-specific peptide and measured by ELISPOT (A) and intracellular cytokine staining (B, C). The number in the pie chart denotes the percentage of triple producers. D shows memory CD8 T cell responses. Memory CD8 T cell proliferation to Zaire GP was assessed in mice immunized with formulated Ad-CAGoptZGP by IN route 42 days after treatment. A decrease in CFSE staining denotes cell division/expansion. Data reflect average values±the standard error of the mean for four mice per group. *indicates a significant difference with respect to the Naive/unformulated group, *p<0.05, **p<0.01, one-way ANOVA, Bonferroni/Dunn post-hoc analysis.

FIGS. 20A-20D show the results of the protective efficiency of formulated vaccine following IN administration in guinea pigs with mucosal PEI. Naive guinea pigs and those with prior exposure to adenovirus serotype 5 via the nasal route (indicated by IN PEI, n=5) were challenged 28 days after immunization with a lethal dose of 1,000 pfu guinea pig-adapted Ebola Zaire (1,000×LD$_{50}$) by intraperitoneal injection. (A) Samples from individual guinea pigs were evaluated for the presence of ZGP-specific IgG subclasses and IgM by ELISA (OD at 450 nm). (B) Kaplan-Meier survival curve. (C) Body weight profile after challenge. (D) Serum alanine (ALT) and aspartate (AST) aminotransferase levels post-challenge. Data reflect average values±the standard error of the mean for five mice per group. * indicates a significant difference with respect to the Naive/unformulated group. *, p<0.05, , p<0.01, *, p<0.001, one-way ANOVA, Bonferroni/Dunn post hoc analysis.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to vaccine compositions that may be administered to a subject via the buccal and/or sublingual mucosa. In some embodiments, the present disclosure also relates to methods for administration and preparation of such vaccine compositions.

The buccal and the sublingual mucosa are attractive for the delivery of medicinal compounds and have largely been uninvestigated in the context of protective immunization. The sublingual and the buccal epithelium are highly vascularized, allowing direct entry into the systemic circulation, avoiding pre-systemic metabolism of antigen in the gastrointestinal tract. They harbor a dense lattice of professional antigen presenting cells (APCs), contain many T lymphocytes and directly access mucosal-associated lymphoid tissues. One of the many advantages of the present disclosure, many of which are not discussed herein, is that a vaccine composition of the present disclosure may be administered by direct application to the cheek (buccal) or under the tongue (sublingual), which may then induce a strong protective systemic and mucosal immune response. Furthermore, in those embodiments where the vaccine is a recombinant adenovirus ("Ad")-based vaccine, it may be administered via the buccal and/or sublingual mucosa with significant potential for successful vaccination of those with pre-existing immunity to Ad5. Pre-existing immunity to Ad5 is a global phenomenon and is currently the most significant limitation to the use of these vectors.

The buccal and sublingual mucosa contain an immobile expanse of smooth muscle upon which of a variety of dosage forms such as lozenges, gels, patches and films can reside (Pather, 2008). This supports an epithelium of 40-50 layers of actively dividing squamous, non-keratinized cells (Wertz, 1991). Although this layer is the most significant barrier to the absorption of large molecules though the cheek, cell turnover is slow (4-14 days), allowing for continued release of antigen (Hill, 1984). Reagents that aid absorption of large molecules across the mucosa (surfactants, cyclodextrins, polyacrlyates) and polymers that facilitate interaction with the surface (polycarbophil, carboxymethyl cellulose) also protect labile molecules from degradation at ambient temperatures (Hassan, 2010; Shojaei, 1998). Accordingly, the present disclosure is also innovative in that it promotes a delivery method that could improve vaccine potency and physical stability at ambient temperatures.

In some embodiments, the present disclosure provides a vaccine composition comprising an antigen dispersed within an amorphous solid. As used herein, the term "antigen" means a substance that induces a specific immune response in a host animal. The antigen may comprise a whole organism, killed, attenuated or live (including killed, attenuated or inactivated bacteria, viruses, fungi, parasites, prions or other microbes); a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternatively, the antigen may comprise a toxin or antitoxin.

In general, an amorphous solid suitable for use in the present disclosure should be dissolvable upon contact with an aqueous liquid, such as a saliva. In some embodiments, amorphous solids suitable for use in the present disclosure may be formed from any sugar, sugar derivative or combination of sugars/derivatives so long as the sugar and/or derivative is prepared as a liquid solution at a concentration that allows it to flow freely when poured but also forms an amorphous phase at ambient temperatures on a physical surface that facilitates this process, such as aluminum or Teflon. Examples of suitable sugars may include, but are not limited to glucose, dextrose, fructose, lactose, maltose, xylose, sucrose, corn sugar syrup, sorbitol, hexitol, maltilol, xylitol, mannitol, melezitose, raffinose, and a combination thereof. While not being bound to any particular theory, it is believed that sugars minimize interaction of the antigen with water during storage and drying, in turn, preventing damage to the three dimensional shape of the antigen due to crystal formation during the drying process and subsequent loss of efficacy. An example of the surface characteristics of an amorphous solid is illustrated in FIG. 15C. In some embodiments, an amorphous solid suitable for use in the present disclosure may have a thickness of about 0.05 millimeters to about 5 millimeters.

In addition, in some embodiments, certain sugars may also function as a binder which may provide "substance" to pharmaceutical preparations that contain small quantities of very potent medications for ease of handling/administration. They may also hold components together or promote binding to surfaces (like the film backing) to ease drug delivery and handling. Lastly, they may also contribute to the overall pharmaceutical elegance of a preparation by forming uniform glasses upon drying.

In certain embodiments, the vaccine compositions of the present disclosure also may comprise a water-soluble polymer including, but not limited to, carboxymethyl cellulose, carboxyvinyl polymers, high amylose starch, hydroxyethyl cellulose, hydroxypropyl cellulose, hydroxypropyl methylcellulose, methylmethacrylate copolymers, polyacrylic acid, polyvinyl alcohol, polyvinyl pyrrolidone, pullulan, sodium alginate, poly(lactic-co-glycolic acid), poly(ethylene) oxide, poly(hydroxyalkanoate) and a combination thereof.

Furthermore, in some embodiments, the vaccine compositions of the present disclosure may further comprise one or more oils, polyalcohols, surfactants, permeability enhancers, and/or edible organic acids. Examples of suitable oils may include, but are not limited to, eucalyptol, menthol, vacrol, thymol, methyl salicylate, verbenone, eugenol, gerianol and a combination thereof. Examples of suitable polyalcohols may include, but are not limited to, glycerol, polyethylene glycol, propylene glycol, and a combination thereof. Examples of suitable edible organic acids may include, but are not limited to, citric acid, malic acid, tartaric acid, fumaric acid, phosphoric acid, oxalic acid, ascorbic acid and a combination thereof. Examples of suitable surfactants may include, but are not limited to, difunctional block copolymer surfactants terminating in primary hydroxyl groups, such as Pluronic® F68 commercially available from BASF, poly (ethylene) glycol 3000, dodecyl-β-D-maltopyranoside, disodium PEG-4 cocamido MIPA-sulfosuccinate ("DMPS"), etc. It is believed that certain surfactants may minimize interaction of the antigen with itself and other antigens and subsequent formation of large aggregated particles that cannot effectively enter and be processed by target and antigen presenting cells. They may also be capable of weakening cell membranes without causing permanent damage and, through this mechanism, promote uptake of large particles though rugged biological membranes such as the buccal mucosa.

A vaccine composition of the present disclosure further comprises an antigen. Antigens suitable for use in the present disclosure may include any antigen for which cellular and/or humoral immune responses are desired, including antigens derived from viral, bacterial, fungal and parasitic pathogens and prions that may induce antibodies, T-cell helper epitopes and T-cell cytotoxic epitopes. Such antigens include, but are not limited to, those encoded by human and animal viruses and can correspond to either structural or non-structural proteins. Furthermore, the present disclosure contemplates vaccines made using antigens derived from any of the antigen sources discussed below and those that use these sources as potential delivery devices or vectors. For example, in one specific embodiment, recombinant adenovirus may be used to deliver Ebola antigens for immunization against Ebola infection.

Antigens useful in the present disclosure may include those derived from viruses including, but not limited to, those from the family Arenaviridae (e.g., Lymphocytic choriomeningitis virus), Arterivirus (e.g., Equine arteritis virus), Astroviridae (Human astrovirus 1), Birnaviridae (e.g., Infectious pancreatic necrosis virus, Infectious bursal disease virus), Bunyaviridae (e.g., California encephalitis virus Group), Caliciviridae (e.g., Caliciviruses), Coronaviridae (e.g., Human coronaviruses 299E and OC43), Deltavirus (e.g., Hepatitis delta virus), Filoviridae (e.g., Marburg virus, Ebola virus), Flaviviridae (e.g., Yellow fever virus group, Hepatitis C virus), Hepadnaviridae (e.g., Hepatitis B virus), Herpesviridae (e.g., Epstein-Bar virus, Simplexvirus, Varicellovirus, Cytomegalovirus, Roseolovirus, Lymphocryptovirus, Rhadinovirus), Orthomyxoviridae (e.g., Influenzavirus A, B, and C), Papovaviridae (e.g., Papillomavirus), Paramyxoviridae (e.g., Paramyxovirus such as human parainfluenza virus 1, Morbillivirus such as Measles virus, Rubulavirus such as Mumps virus, Pneumovirus such as Human respiratory syncytial virus), Picornaviridae (e.g., Rhinovirus such as Human rhinovirus 1A, Hepatovirus such Human hepatitis A virus, Human poliovirus, Cardiovirus such as Encephalomyocarditis virus, Aphthovirus such as Foot-and-mouth disease virus O, Coxsackie virus), Poxyiridae (e.g., Orthopoxvirus such as Variola virus or monkey poxvirus), Reoviridae (e.g., Rotavirus such as Groups A-F rotaviruses), Retroviridae (Primate lentivirus group such as human immunodeficiency virus 1 and 2), Rhabdoviridae (e.g., rabies virus), Togaviridae (e.g., Rubivirus such as Rubella virus), Human T-cell leukemia virus, Murine leukemia virus, Vesicular stomatitis virus, Wart virus, Blue tongue virus, Sendai virus, Feline leukemia virus, Simian virus 40, Mouse mammary tumor virus, Dengue virus, HIV-1 and HIV-2, West Nile, H1N1, SARS, 1918 Influenza, Tick-borne encephalitis virus complex (Absettarov, Hanzalova, Hypr), Russian Spring-Summer encephalitis virus, Congo-Crimean Hemorrhagic Fever virus, Junin Virus, Kumlinge Virus, Marburg Virus, Machupo Virus, Kyasanur Forest Disease Virus, Lassa Virus, Omsk Hemorrhagic Fever Virus, FIV, SIV, Herpes simplex 1 and 2, Herpes Zoster, Human parvovirus (B19), Respiratory syncytial virus, Pox viruses (all types and serotypes), Coltivirus, Reoviruses—all types, and/or Rubivirus (rubella).

Antigens useful in the present disclosure may include those derived from bacteria including, but not limited to, *Streptococcus agalactiae, Legionella pneumophilia, Streptococcus pyogenes, Escherichia coli, Neisseria gonorrhosae, Neisseria meningitidis, Pneumococcus, Hemophilis influenzae* B, *Treponema pallidum,* Lyme disease spirochetes, *Pseudomonas aeruginosa, Mycobacterium leprae, Brucella abortus, Mycobacterium tuberculosis, Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium, M. pneumoniae, Candida albicans, Cryptococcus neoformans, Histoplasma capsulatum, Coccidioides immitis, Blastomyces dermatitidis, Aspergillus fumigatus, Penicillium marneffei, Bacillus anthracis, Bartonella, Bordetella pertussis, Brucella*—all serotypes, *Chlamydia trachomatis, Chlamydia pneumoniae, Clostridium botulinum*—anything from *Clostridium* serotypes, *Haemophilus influenzae, Helicobacter pylori, Klebsiella*—all serotypes, *Legionella*—all serotypes, *Listeria, Mycobacterium*—all serotypes, *Mycoplasma*—human and animal serotypes, *Rickettsia*—all serotypes, *Shigella*—all serotypes, *Staphylococcus aureus, Streptococcus—S. pneumoniae, S. pyogenes, Vibrio cholera, Yersinia enterocolitica,* and/or *Yersinia pestis.*

Antigens useful in the present disclosure may include those derived from parasites including, but not limited to, *Ancylostoma* human hookworms, *Leishmania*—all strains, *Microsporidium, Necator* human hookworms, *Onchocerca* filarial worms, *Plasmodium*—all human strains and simian species, *Toxoplasma*—all strains, *Trypanosoma*—all serotypes, and/or *Wuchereria bancrofti* filarial worms.

In another embodiment, an antigen is an aberrant protein derived from a sequence which has been mutated. Such antigens may include those expressed by tumor cells or aberrant proteins whose structure or solubility leads to the formation of an aggregation-prone product and cause disease. Examples of aberrant proteins may include, but are not limited to, Alzheimer's amyloid peptide, SOD1, presenillin 1 and 2, α-synuclein, amyloid A, amyloid P, CFTR, transthyretin, amylin, lysozyme, gelsolin, p53, rhodopsin, insulin, insulin receptor, fibrillin, α-ketoacid dehydrogenase, collagen, keratin, PRNP, immunoglobulin light chain, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, dentaorubral pallidoluysian atrophy-associated protein, maltose-binding protein, ABC transporter, glutathione-S-transferase, and thioredoxin.

In one embodiment, a vaccine composition comprising an amorphous solid may be made by preparing a solution comprising a sugar, sugar derivative or combination of sugars/derivatives in a buffer and optionally other additives previously mentioned. In some embodiments, a sugar, sugar derivative or combination of sugars/derivatives may be present in the solution in an amount up to about 60% by weight of the solution. In some embodiments, an additive may be present in an amount of about 5% or less by weight of the solution. In general, the solution comprising the sugar, sugar derivative or combination of sugars/derivatives is made at a concentration higher than the desired final concentration to compensate for any dilution that may occur when the antigen is added. The desired antigen may be added to the solution at a concentration known to induce the desired immune response. The mixture may then be stirred at ambient temperature until a substantially homogeneous mixture is obtained. In some embodiments, the mixture may then be briefly sonicated under cooled conditions, e.g. 4° C., to remove any air bubbles that may have developed. In other embodiments, the mixture may be slightly heated, e.g., heated to 40° C. or below, slightly cooled, and in some instances may be frozen. In some embodiments, a vaccine composition of the present disclosure may be made without freeze drying or spray draying. The final formulation may then be cast onto a flat backing surface in a laminar flow hood and allowed to form an amorphous solid at ambient temperatures (15-20° C.). Examples of suitable backing surfaces may include, but are not limited to, thin layers of aluminum, Teflon, silicate, polyetheretherketone, low density polyethylene, ethyl cellulose, etc. Once the process is complete the vaccine composition can be peeled from the backing and placed in the mouth for immunization purposes and/or stored at ambient temperature for up to one year from manufacture.

In another embodiment, a vaccine composition of the present disclosure may be made by contacting an amorphous solid with an antigen, or optionally, mixing an antigen with one or more excipients (surfactants, sugars, starches, etc.) and contacting the amorphous solid with the mixture so as to dispose the antigen within the amorphous solid. In some embodiments, the mixture is then allowed to dry, which is then ready for administration.

In some embodiments, vaccine compositions of the present disclosure may further comprise a protective layer disposed on a surface of an amorphous solid comprising an antigen. Exemplary protective layers may include, but are not limited to, an additional layer(s) of film, such as polyethylene, polyurethane, polyether etherketone, etc., and/or an additional layer(s) of an amorphous solid that does not contain any antigen. One example of a vaccine composition comprising a protective layer is illustrated in FIG. 1. In some embodiments, the use of a protective layer of film may minimize the absorption of moisture from the atmosphere and prevent adherence to other objects during storage and/or transport. Prior to administration, this layer may be removed from the device (e.g., by peeling the layer off) and may be discarded, as shown in FIG. 2.

The amount of antigen that may be used in a vaccine composition of the present disclosure may vary greatly depending upon the type of antigen used, the formulation used to prepare the vaccine composition, the size of the amorphous solid, the solubility of the antigen, etc. One of ordinary skill in the art with the benefit of this disclosure will be able to determine a suitable amount of antigen to include in a vaccine composition of the present disclosure. In one embodiment, a vaccine composition may comprise about $1\times10^6$ to about $1\times10^{13}$ virus particles for a virus-based vaccine or about $1\times10^3$ to about $1\times10^{13}$ colony forming units for a bacteria-based vaccine.

It is also important to note that when formulating a vaccine composition of the present disclosure one must also consider any toxicity and/or adverse effects. Furthermore, in an effort to create a stable vaccine composition, it may also be important to identify a ratio of ingredients that interacts with water and the antigen in a manner that prevents crystallization during drying. Formation of water crystals will puncture the virus coat or bacterial wall and compromise the overall potency of the vaccine. Formulations that do this to the highest degree are said to form glasses.

In some embodiments, a glass plate can be used for casting of the vaccine composition, which can be dried under a controlled, laminar flow of air at room temperature, or under refrigerated conditions. Similarly, vaccine compositions suitable for use in the present disclosure can be prepared in a single-layer or multi-layers.

In general, the vaccine compositions of the present disclosure may be formulated so as to dissolve in a relatively short period of time, from about 5 to 60 seconds. When administered, a vaccine composition of the present disclosure may be handled by a portion of the composition that does not contain an antigen and may be placed in the upper pouch of the cheek for buccal delivery, as shown in FIG. 3, or far under the tongue for sublingual delivery (not shown).

In some embodiments, the compositions and methods of the present disclosure may also be used as a means for treating a variety of malignant cancers. For example, the vaccine compositions of the present disclosure can be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc.; any of the various tyrosinases; MART 1 (melanoma antigen recognized by T cells), mutant ras; mutant p53; p97 melanoma antigen; CEA (carcinoembryonic antigen), among others.

To facilitate a better understanding of the present invention, the following examples of certain aspects of some embodiments are given. In no way should the following examples be read to limit, or define, the entire scope of the invention.

EXAMPLE 1

Recombinant adenovirus serotype 5 ($5\times10^9$ infectious virus particles) was placed in various formulations or saline (control solution) and air dried on 18 mm sterile polyurethane film disks. FIGS. 4A-4D depict representative images of dried formulations of the virus-based vaccine for buccal administration after storage at room temperature (25° C.) for one month. More specifically, FIG. 4A is virus dried in phosphate buffered saline, pH 7.4. This buffer was the base for all formulations tested. Note obvious salt crystals that formed on the film after drying. FIG. 4B is virus dried in a formulation consisting of melezitose (10 mg/ml), mannitol (40 mg/ml) and Pluronic F68 (0.001%) in phosphate buffered saline. Sizable crystals were detected on the edge of the film while the formulation appeared to form a fairly stable glass in the center of the film. FIG. 4C is virus dried in a formulation consisting of melezitose (10 mg/ml), mannitol (40 mg/ml) and poly(ethylene) glycol (PEG) 3000 (0.1%) in phosphate buffered saline. Replacing the Pluronic F68 in the formulation in FIG. 4B to PEG promoted significant crystal formation on the majority of the film. FIG. 4D is virus dried in a formulation consisting of melezitose (10 mg/ml), sorbitol (40 mg/ml) and poly(ethylene) glycol (PEG) 3000 (0.1%) in phosphate buffered saline. This formulation formed a nice glass with minimal crystal formation upon drying.

Formulations Can Preserve Virus Infectivity After Dry Storage for One Month. Recombinant adenovirus serotype 5 ($5\times10^9$ infectious virus particles) containing a maker transgene, beta-galactosidase, was placed in formulations, spotted on 18 mm sterile polyurethane film disks and air-dried for 14 hours at room temperature (25° C.). Each film was then stored in a clean, dry container at room temperature for one month. At that time, each film was washed with 300 microliters of sterile saline and the infectious titer of virus obtained in the wash determined by a standard limiting dilution assay on HeLa cells. Sixteen hours after infection, cells were stained with the chromogenic substrate, 5-bromo-4-chloro-3-indolyl-beta-galactoside, for 12 hours at 37° C. in the dark. Blue lack cells were tallied from a minimum of 10 microscope fields (approximately 4,800 cells) and infectious titer calculated according to standard protocols.

As shown in FIG. 5, infectious virus formulated in saline alone could not be detected in any samples prepared, dried and stored for one month. Formulation 1 consisted of virus dried in a formulation consisting of melezitose (10 mg/ml), mannitol (40 mg/ml) and Pluronic F68 (0.001%) in phosphate buffered saline. $1.92\times10^7$ infectious virus particles/ml were found in this formulation one month after storage. Although this concentration was significantly reduced from the concentration of the preparation originally put on the film ($5\times10^9$ infectious virus particles/ml, Initial on the graph), it is important to note that sizable crystals were detected on the edge of the film while the formulation appeared to form a fairly stable glass in the center (FIG. 4B).

Formulation 2 consisted of virus dried in a formulation consisting of melezitose (10 mg/ml), mannitol (40 mg/ml) and poly(ethylene) glycol (PEG) 3000 (0.1%) in phosphate buffered saline. Replacing the Pluronic F68 in Formulation 1 with PEG promoted significant crystal formation on the majority of the film (FIG. 4C) and subsequent loss of infectious titer.

Formulation 3 consisted of virus dried in a formulation consisting of melezitose (10 mg/ml), mannitol (40 mg/ml) and poly(ethylene) glycol (PEG) 3000 (1%) in phosphate buffered saline. Increasing the concentration of PEG in the formulation did not improve infectious titer of virus recovered from the film.

Formulation 4 consisted of virus dried in a formulation consisting of melezitose (10 mg/ml), mannitol (40 mg/ml) and dodecyl-β-D-maltopyranoside (DMPS, 100 nM) in phosphate buffered saline. Replacing the PEG in Formulation 3 with DMPS significantly improved recovery of virus after drying. The infectious titer of this preparation after one month was $3.18\times10^9$ infectious virus particles/ml.

Formulation 6 consisted of virus dried in a formulation consisting of melezitose (10 mg/ml), sorbitol (40 mg/ml) and PEG (0.1%) in phosphate buffered saline. Infectious titer of this preparation was not compromised during drying and storage since the infectious titer was not significantly different from the original concentration one month after storage ($6.05\times10^9$ vs. $5.19\times10^9$ infectious virus particles/ml, Initial). It should be noted that this formulation formed a near perfect glass (FIG. 4D). Initial. Infectious titer of stock virus preparation prior to addition to film for drying. Table 1 below is a summary of the various formulations.

TABLE 1

| Formulation | Contents |
| --- | --- |
| Phosphate Buffered Saline (pH 7.4) | Base for all formulations |
| Formulation #1 | Melezitose (10 mg/ml), Mannitol (40 mg/ml) and Pluronic F68 (0.001%) |
| Formulation #2 | Melezitose (10 mg/ml), Mannitol (40 mg/ml), poly(ethylene) glycol (PEG) (0.1%) |
| Formulation #3 | Melezitose (10 mg/ml), mannitol (40 mg/ml), poly(ethylene) glycol (PEG) (1%) |
| Formulation #4 | Melezitose (10 mg/ml), mannitol (40 mg/ml), dodecyl-β-D-maltopyranoside(100 nM) |
| Formulation #6 | Melezitose (10 mg/ml), sorbitol (40 mg/ml), PEG (0.1%) |

Formulations Preserve Bacteria During Drying and Promote Growth Upon Rehydration. *Escherichia coli* (strain DH5α, $1.93 \times 10^5$ colony forming units/ml) was spotted on 18 mm sterile polyurethane film disks and air-dried for 6 hours at room temperature (25° C.). The following day, each film was washed with 300 microliters of sterile saline and the amount of living bacteria obtained in the wash determined by a dilution assay on agar plates containing a selective antibiotic. Colonies were counted 16 hours after plating and concentration of bacteria calculated according to standard protocols.

Figure 6:
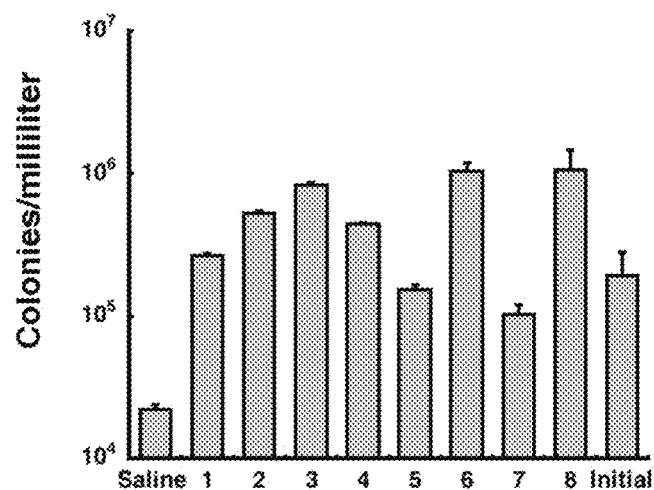
FIG. 6 is a graph depicting the ability of various formulations to preserve bacteria during drying and to promote growth upon rehydration.

As shown in FIG. 6, drying bacteria in saline (pH 7.4) alone overnight at room temperature reduced bacterial concentrations from $1.93 \times 10^5$ colonies/ml (Initial on graph) to $2.24 \times 10^4$ colonies/ml. Formulation 1 consisted of bacteria dried in a formulation consisting of melezitose (10 mg/ml), sorbitol (40 mg/ml) and PEG (1%) in phosphate buffered saline. There was no significant loss of bacteria upon rehydration ($2.66 \times 10^5$ colonies/ml) with respect to the initial concentration of the preparation ($1.93 \times 10^5$ colonies/ml, Initial on graph).

Formulation 2 consisted of bacteria dried in a formulation consisting of melezitose (10 mg/ml), sorbitol (40 mg/ml) and Pluronic F68 (0.001%) in phosphate buffered saline. This formulation promoted bacterial growth upon rehydration with a slight increase in bacterial count noted ($5.27 \times 10^5$ colonies/ml).

Formulation 3 consisted of bacteria dried in a formulation consisting of melezitose (40 mg/ml), sorbitol (40 mg/ml) and PEG (1%) in phosphate buffered saline. This formulation also promoted bacterial growth upon rehydration with an increase in bacterial count noted ($8.38 \times 10^5$ colonies/ml).

Formulation 4 consisted of bacteria dried in a formulation consisting of melezitose (40 mg/ml), sorbitol (40 mg/ml) and Pluronic F68 (0.001%) in phosphate buffered saline. This formulation promoted bacterial growth upon rehydration with a slight increase in bacterial count noted ($4.43 \times 10^5$ colonies/ml).

Formulation 5 consisted of bacteria dried in a formulation consisting of sucrose (10 mg/ml), sorbitol (40 mg/ml) and PEG (1%) in phosphate buffered saline. This formulation did not significantly alter bacteria concentration upon rehydration ($1.55 \times 10^5$ colonies/ml).

Formulation 6 consisted of bacteria dried in a formulation consisting of sucrose (10 mg/ml), sorbitol (40 mg/ml) and Pluronic F68 (0.001%) in phosphate buffered saline. This formulation was one of the most successful, preserving bacteria and facilitating growth upon reconstitution to a concentration of ($1.04 \times 10^6$ colonies/ml).

Formulation 7 consisted of bacteria dried in a formulation consisting of sucrose (40 mg/ml), sorbitol (40 mg/ml) and PEG (1%) in phosphate buffered saline. This formulation adequately preserved bacteria upon drying with a concentration of $1.04 \times 10^5$ colonies/ml noted upon rehydration.

Formulation 8 consisted of bacteria dried in a formulation consisting of sucrose (40 mg/ml), sorbitol (40 mg/ml) and Pluronic F68 (0.001%) in phosphate buffered saline. This formulation was successful, preserving bacteria and facilitating growth upon reconstitution to a concentration of ($1.06 \times 10^6$ colonies/ml). Initial. Average bacterial concentration of stock preparations prior to addition to film for drying.

TABLE 2

| Formulation | Contents |
| --- | --- |
| Phosphate Buffered Saline (pH 7.4) | Base for all formulations |
| Formulation #1 | Melezitose (10 mg/ml), sorbitol (40 mg/ml), PEG (1%) |
| Formulation #2 | Melezitose (10 mg/ml), sorbitol (40 mg/ml), Pluronic F68 (0.001%) |
| Formulation #3 | Melezitose (40 mg/ml), sorbitol (40 mg/ml), PEG (1%) |
| Formulation #4 | Melezitose (40 mg/ml), sorbitol (40 mg/ml), Pluronic F68 (0.001%) |
| Formulation #5 | Sucrose (10 mg/ml), sorbitol (40 mg/ml), PEG (1%) |
| Formulation #6 | Sucrose (10 mg/ml), sorbitol (40 mg/ml), Pluronic F68 (0.001%) |
| Formulation #7 | Sucrose (40 mg/ml), sorbitol (40 mg/ml), PEG (1%) |
| Formulation #8 | Sucrose (40 mg/ml), sorbitol (40 mg/ml), Pluronic F68 (0.001%) |

Figures 7A, 7B, 7C, 7D, 7E, 7F:
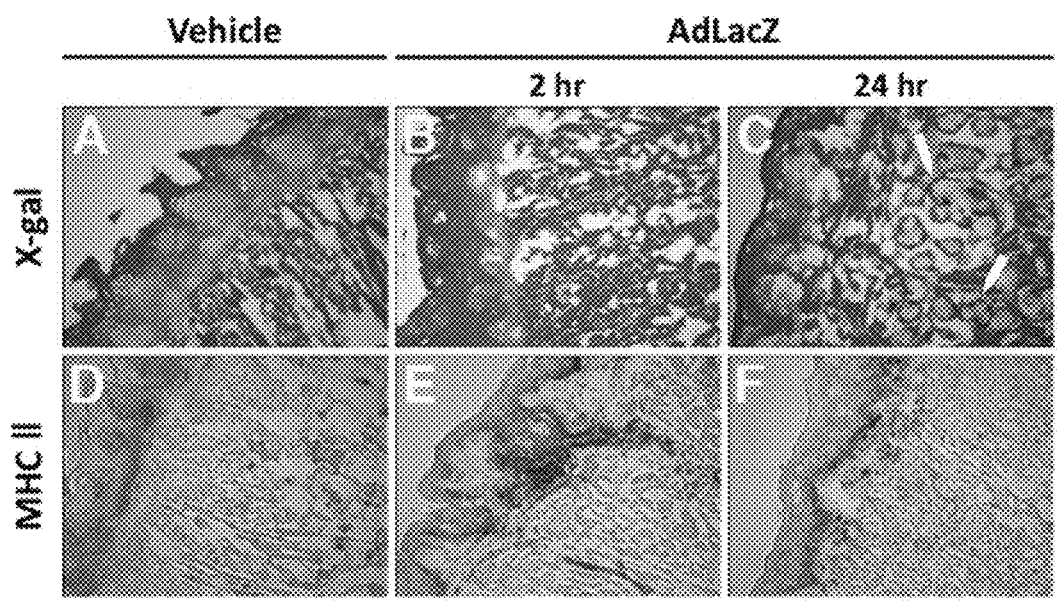
FIGS. 7A-7F are images depicting buccal tissue excised from B10.Br mice immunized with recombinant adenovirus.

Adenovirus Serotype 5-Based Vaccines Effectively Transduce the Oral Mucosa after Sublingual Administration and Stimulates Migration of Antigen Presenting Cells to the Site of Vaccination. Six week old B10.Br mice were immunized by placing $1 \times 10^8$ infectious particles of a recombinant adenovirus containing the marker gene, beta-galactosidase (AdlacZ) in a volume of 10 μl with a micropipette. Animals were sacrificed 2 (FIGS. 7B and 7E) and 24 (FIGS. 7C and 7F) hours after immunization and submandibular and buccal tissue excised and placed in OCT freezing medium. Cryosections taken 2 hours after immunization (FIG. 7B) did not display notable transgene expression with respect to sections taken from mice given saline (FIG. 7A). In contrast, sections taken 24 hours after treatment contained concentrated patches of the blue substrate of the beta-galactosidase transgene throughout the tissue (white arrows, FIG. 7C).

Antigen presenting cells at the site of administration are a key determinant of the potency of a vaccine as they can either prime CD8 effector T cells or favor development of mucosal and systemic tolerance. Additional histochemical staining of sections for MHC II surface antigens reveal concentrated patches of MHCII cells such as macrophages and dendritic cells at the site of vaccination (FIG. 7E, brown staining for MHC II surface antigens) and the subsequent dispersal of these cells throughout the mucosa 24 hours after immunization (FIG. 7F) at a level higher than that seen in unimmunized animals (FIG. 7D).

Figure 8A:
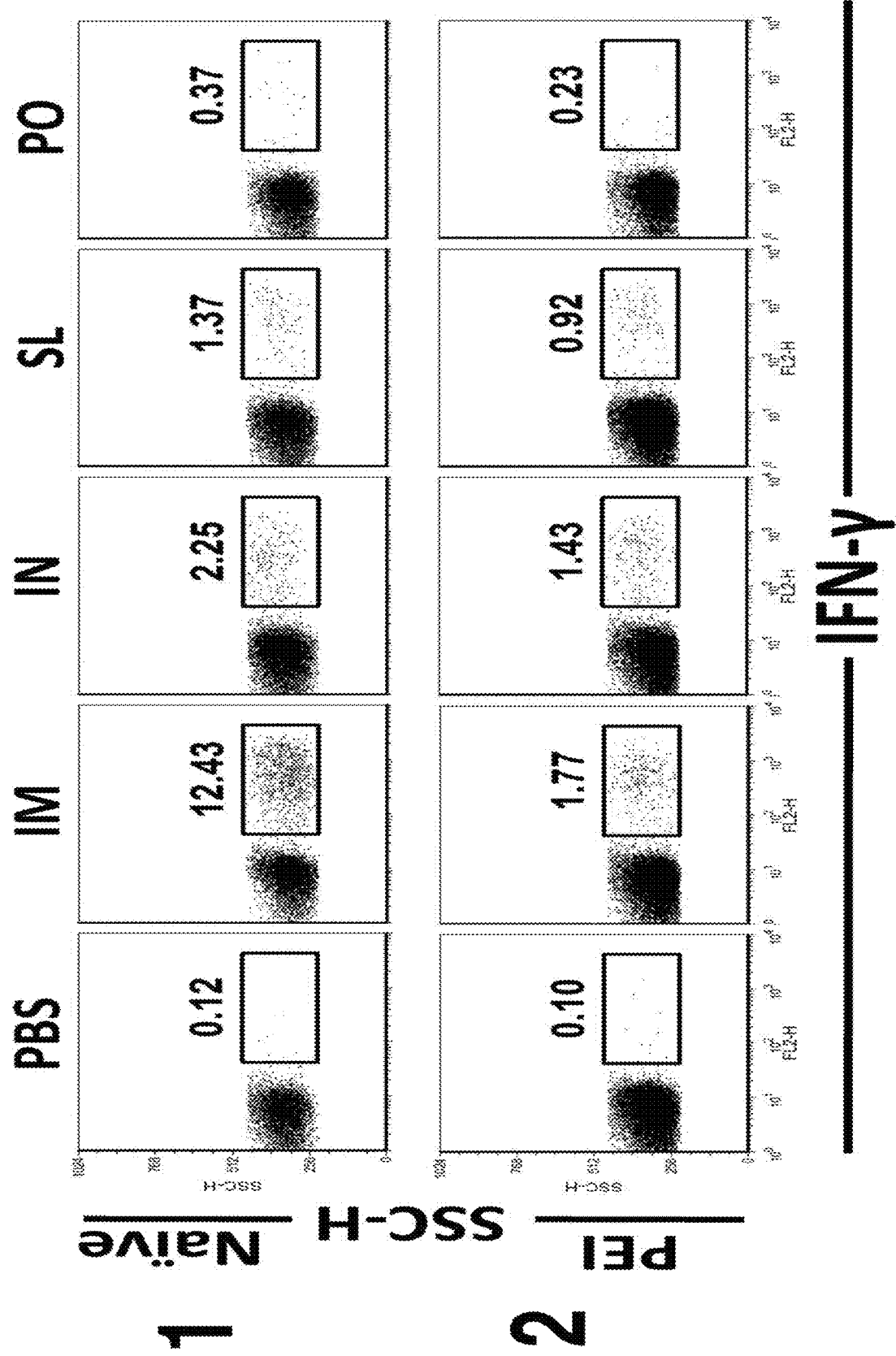
FIG. 8A is an image representing the percentages of the average proportion of each cell population that recognized and was activated by Ebola Zaire glycoprotein for each of the indicated treatment groups.

Sublingual Immunization (S.L.) with an Adenovirus Serotype 5-based vaccine Encoding Ebola Zaire Glycoprotein Produces a T Cell Response Greater than Oral Immunization (P.O.) and Similar to Intranasal Immunization (I.N.) and is Less Affected by Prior Exposure to Adenovirus than Any Other Method of Immunization. B10.Br mice were immunized by various routes with $1 \times 10^8$ infectious particles of a recombinant adenovirus expressing Ebola Zaire glycoprotein. A subset of these mice were given $2.5 \times 10^{11}$ particles of a recombinant adenovirus containing the marker gene, beta-galactosidase, by intramuscular injection 28 days prior to vaccination to induce circulating anti-adenovirus antibodies similar to what is seen in the general public. This group is denoted in FIG. 8A as IM PEI. (Line 2). Mice treated in this manner had an average antibody titer of 1:480 reciprocal dilution prior to vaccination. Mice were sacrificed 10 days after vaccination. Splenocytes were harvested and stimulated with an Ebola glycoprotein-specific peptide and stained with antibodies against CD8 surface proteins and intracellular interferon gamma (IFN-$\gamma$). Activated T cells producing IFN-$\gamma$ were identified by flow cytometry. Percentages written in each box represent the average proportion of each cell population that recognized and was activated by Ebola Zaire glycoprotein in each treatment group.

Figure 8B:
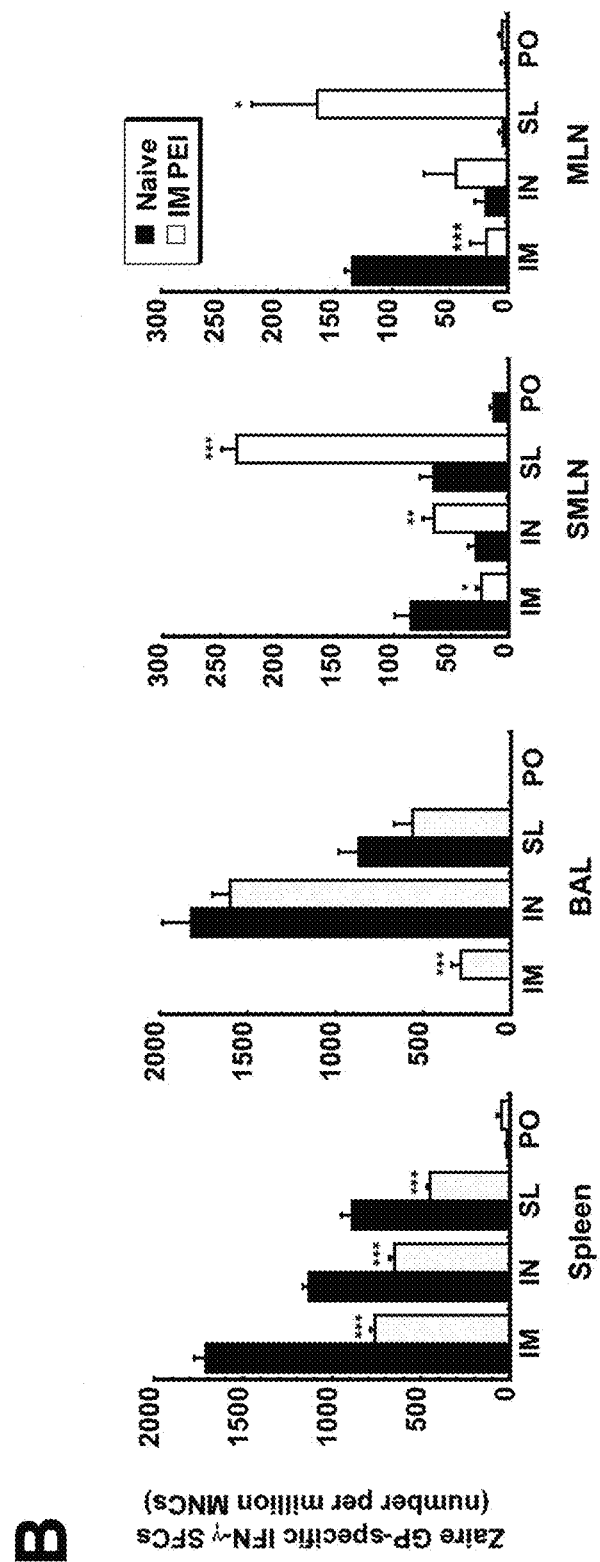
FIG. 8B are graphs depicting the anti-ebola immune response in mice with pre-existing immunity to adenovirus that were immunized by the sublingual route in certain mucosal compartments.

Pre-Existing Immunity to Adenovirus Promotes the Anti-Ebola Immune Response in Mice Immunized by the Sublingual Route in Certain Mucosal Compartments. Mice were treated as described in FIG. 8A. Lymphocytes were harvested from various compartments and analyzed for production of IFN-$\gamma$ production in response to Ebola Zaire glycoprotein by ELISPOT. As shown in FIG. 8B, although pre-existing immunity compromised the response in the spleen in all treatment groups, the response in the bronchioalveolar lavage fluid (BAL) was not compromised by prior exposure to adenovirus in mice vaccinated by the nasal and sublingual routes. Pre-existing immunity also strengthened the anti-Ebola glycoprotein responses in submandibular (SMLN) and mesenteric (MLN) lymph nodes of mice immunized by the nasal and sublingual routes. Key: I.M.—intramuscular, I.N.—intranasal, S.L.—sublingual, P.O.—oral, IM PEI—pre-existing immunity to adenovirus induced by intramuscular injection, BAL—bronchioalveolar lavage fluid, SMLN—submandibular lymph nodes, MLN—mesenteric lymph nodes. *$p<0.05$, $p<0.01$, *$p<0.001$, one-way ANOVA, Bonferroni/Dunn post-hoc analysis.

Sublingual Immunization Significantly Reduces Production of IL-6 in Response to the Adenovirus Vector and Minimizes Toxicity Associated with Adenovirus-Based Vaccines. Systemic administration of recombinant adenoviruses induce a potent innate immune response largely directed against the vector and later against the transgene product. These effects are highlighted by significant increases in serum cytokines (IL-6, IL-12, TNF-$\alpha$) as early as 6 hours after administration. It has also been found that animals with increased levels of these cytokines often do not survive challenge with Ebola. The adenovirus also preferentially distributes to the liver and is rapidly taken up by both Kupffer cells and hepatocytes, which contribute to this effect. Hepatotoxicity can also occur, as indicated by sharp increases in serum transaminases (AST/ALT) 4-7 days after treatment.

Figures 9A, 9B, 9C, 9D:
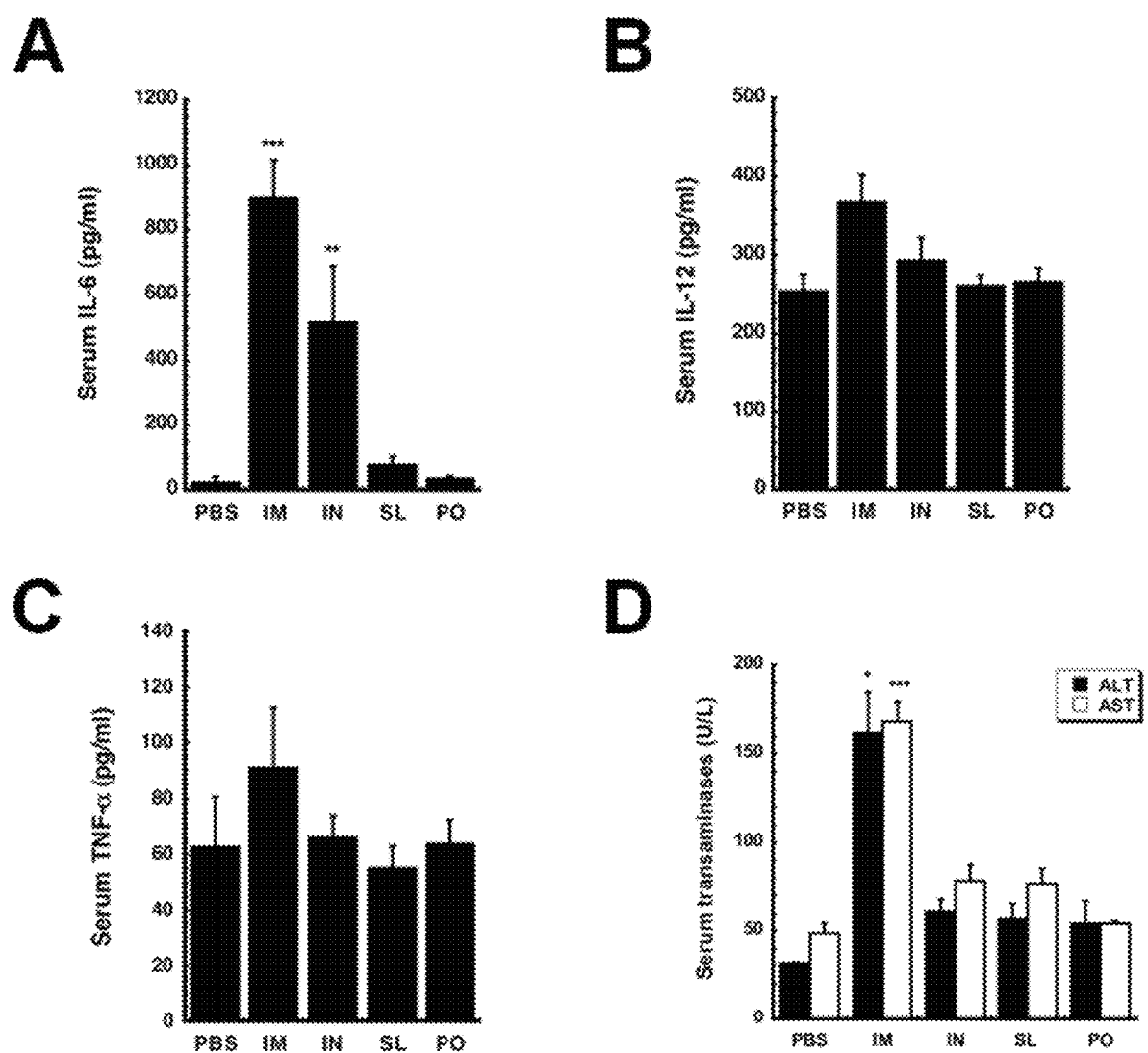
FIG. 9A-9D are graphs depicting various serum levels after immunization by various routes.

FIG. 9A shows serum interleukin 6 (IL-6) levels 6 hours after immunization by various routes. Significant increases in IL-6 were noted in mice vaccinated by the intramuscular (I.M., 90×control (PBS)) and intranasal (I.N., 50×control (PBS)). The amount of this cytokine in samples from mice immunized by the oral and sublingual routes were not significantly different than those given saline (PBS, negative control).

FIG. 9B shows serum IL-12 levels 6 hours after immunization by various routes. The amount of this cytokine in samples from each treatment group was not significantly different than those given saline (PBS, negative control).

FIG. 9C shows serum tumor necrosis factor alpha (TNF-$\alpha$) levels 6 hours after immunization by various routes. The amount of this cytokine in samples from each treatment group was not significantly different than those given saline (PBS, negative control).

FIG. 9D shows serum transaminases 4 days after vaccination. Serum alanine aminotransferase (ALT) and aspartate aminotransferase (AST) levels were significantly elevated in mice immunized by the intramuscular route. These enzymes were not significantly elevated in mice immunized by the nasal, oral or sublingual routes. Key: I.M.—intramuscular, I.N.—intranasal, S.L.—sublingual, P.O.—oral, IM *$p<0.05$, $p<0.01$, *$p<0.001$, one-way ANOVA, Bonferroni/Dunn post-hoc analysis.

Sublingual Immunization Can Induce Strong, Long-Lasting T Cell-Mediated Immune Responses. CD8 T cell memory is a crucial component of protective immunity against microbial infection. Memory T cells, when present, can respond with enhanced kinetics and magnitude to ensure protection against re-infection. The presence of immunological memory to Ebola glycoprotein was assessed in mice immunized with recombinant adenovirus by various routes 42 days after treatment.

Figures 10A, 10B:
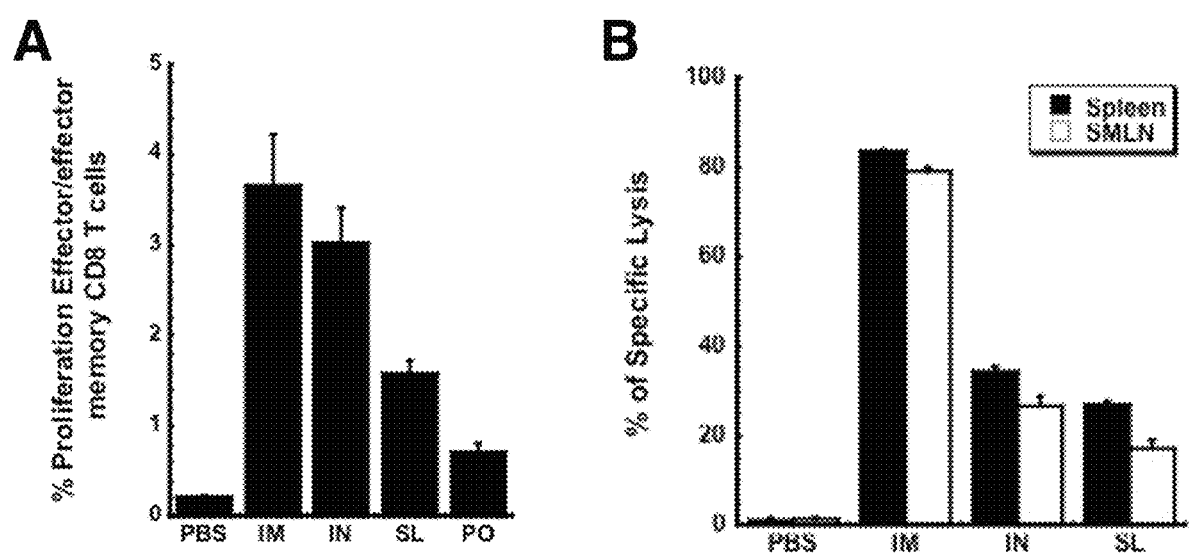
FIGS. 10A is graph depicting the CD8 effector memory T cell response to an Ebola glycoprotein-specific peptide after immunization by various routes
FIG. 10B is a graph depicting the cytolytic T memory response to an Ebola glycoprotein-specific peptide after immunization by various routes.

FIG. 10A depicts CD8 effector memory T cell response to an Ebola glycoprotein-specific peptide after immunization by various routes as determined by an in vitro proliferation assay. CD8 memory T cells are a heterogeneous population that can be broadly segregated into two general subsets: central memory and effector memory T cells. Central memory cells are mainly located in lymphoid organs, expressing high levels of CD44 and CD62L ($CD44^{hi}CD62L^{hi}$), are highly proliferative and require a relatively longer period of activation to achieve cytolytic properties. Effector memory T cells express increased levels of CD44 but markedly reduced levels of CD62L ($CD44^{hi}CD62L^{lo}$), have less proliferative potential, re-circulate preferentially through non-lymphoid tissues, and are immediately cytolytic upon re-exposure to antigen. This latter population of cells was identified in splenocytes of mice vaccinated by various routes stained with carboxyfluorescein diacetate N-succinimidyl ester (CFDA SE), a fluorescent dye that is evenly diluted during cell division upon stimulation with an Ebola glycoprotein-specific peptide for 5 days. Cells were then stained with anti-CD8, CD44 and CD62L antibodies and the ($CD44^{hi}CD62L^{lo}$) population identified by flow cytometry. Mice immunized by the intramuscular route contained the highest number of CD8 effector/effector memory cells. Those immunized by the nasal contained similar levels of memory cells while those immunized by the sublingual and oral routes had the lowest numbers of these cells out of all treatment groups.

FIG. 10B depicts the cytolytic T memory response to an Ebola glycoprotein-specific peptide after immunization by various routes as determined by an in vivo assay. Splenocytes from naïve mice were harvested and divided into to 2 populations. The first was stained with 5 µM CFDA SE (CFSE HIGH) and the second with 0.5 µM of the dye (CFSE LOW). The CFSE HIGH group was pulsed with an Ebola glycoprotein-specific peptide for 45 minutes while the CFSE LOW cells were not. An equal number of cells from each population were then given intravenously to mice immunized with recombinant adenovirus expressing Ebola glycoprotein by various routes 42 days after treatment. Twenty-four hours later, mice were sacrificed and single cell suspensions from spleen and submandibular lymph nodes (SMLN) were generated. Differential CFSE staining patterns were identified in each population by flow cytometry. Significant reductions in the CFSE HIGH population is indicative of recognition and subsequent lysis of these cells in the immunized mice.

Sublingual Immunization Induces Circulating Anti-Ebola Glycoprotein Antibodies in Naïve Mice and those with Prior Exposure to Adenovirus at a Higher Level than Intramuscular Immunization. Serum collected from all mice 42 days after vaccination was heat inactivated, serially diluted in 2 fold increments and placed in 96 well plates coated with recombinant Ebola Zaire glycoprotein. Wells were then incubated with antibodies against mouse antibody subclasses (IgG, IgG1, IgG2a and IgG2b) conjugated to horseradish peroxidase. After the addition of the substrate, p-nitrophenyl phosphate, optical densities (O.D.) of each well were read at 450 nm on a microplate reader. End point titers for each antibody isotype are expressed as the reciprocal loge of the last dilution giving an O.D. of 0.1 unit above background levels.

Figures 11A, 11B:
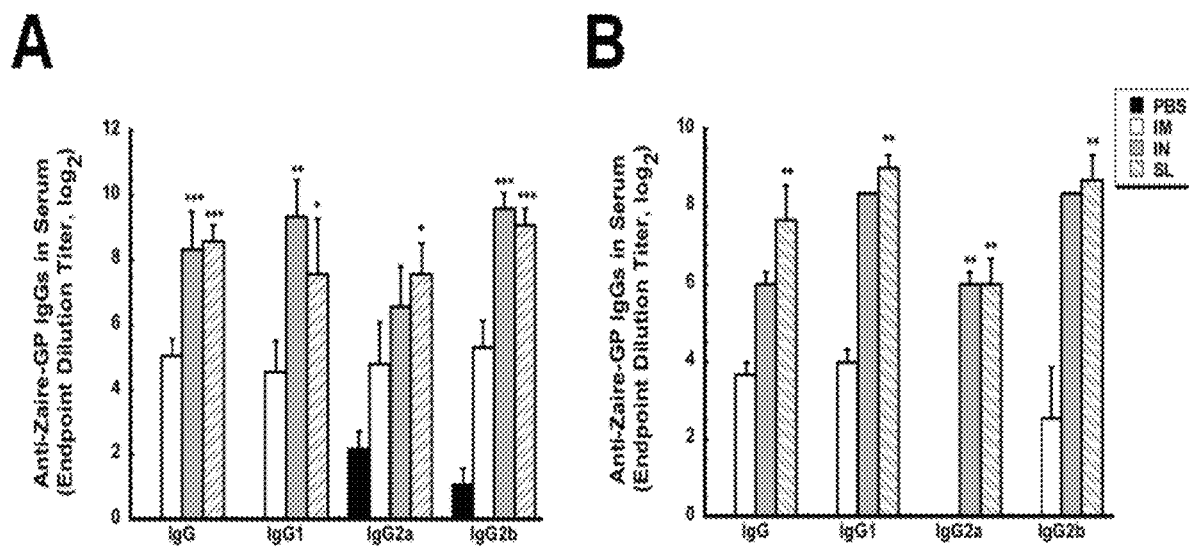
FIGS. 11A-11B are graphs depicting the antibody response against Ebola glycoprotein after immunization by various routes.

FIG. 11A shows that sublingual and intranasal immunization induces production of significantly more circulating anti-Ebola glycoprotein antibodies than intramuscular immunization. For FIG. 11B, pre-existing immunity to adenovirus 5 was established in a subset of these mice by a single intramuscular dose of $2.5 \times 10^{11}$ particles of a recombinant adenovirus containing the marker gene, beta-galactosidase, 28 days prior to vaccination. Mice treated in this manner had an average antibody titer of 1:480 reciprocal dilution prior to vaccination.

The antibody response against Ebola glycoprotein is somewhat strengthened by sublingual immunization of mice with pre-existing immunity to adenovirus 5. Pre-existing immunity blocked the IgG2a response in mice immunized by the intramuscular route. Key: I.M.—intramuscular, I.N.—intranasal, S.L.—sublingual, P.O.—oral, IM *p<0.05, p<0.01, *p<0.001, one-way ANOVA, Bonferroni/Dunn post-hoc analysis.

Sublingual Immunization Induces Significant Amounts of Anti-Ebola Glycoprotein Antibodies in the Bronchioalveolar Lavage Fluid (BAL) of Naïve Mice and Those with Prior Exposure to Adenovirus 5 (IM PEI). Pre-existing immunity was induced as described in FIGS. 8 and 11. Mice treated in this manner had an average antibody titer of 1:480 reciprocal dilution prior to vaccination, which is similar to what is observed in the general population. Bronchoalveolar lavage (BAL) fluid was collected from mice vaccinated by various routes in situ with a 20-gauge catheter inserted into the proximal trachea, flushing the lower airways three times with 1 milliliter of L15 culture media 42 days after immunization. Samples were diluted in 2-fold increments in 96 well plates as described for serum in FIG. 8.

Figure 12:
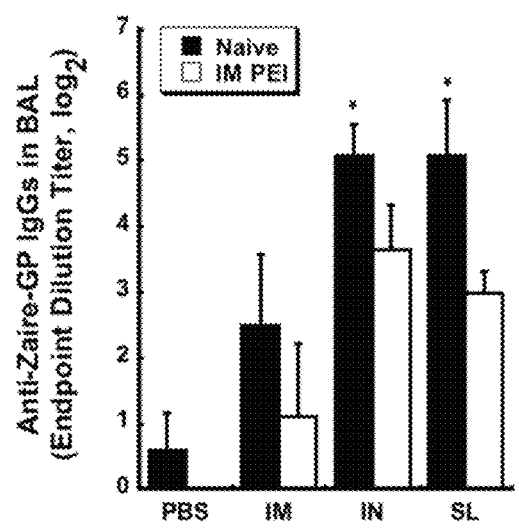
FIG. 12 is a graph depicting the antibody response against Ebola glycoprotein after immunization by various routes.

As shown in FIG. 12, samples obtained from naïve mice immunized by the sublingual and nasal routes were significantly higher than those immunized by the intramuscular route. Pre-existing immunity to adenovirus also did not significantly compromise antibody levels in BAL of mice immunized by these routes (I.N., S.L.). Key: I.M.—intramuscular, I.N.—intranasal, S.L.—sublingual, P.O.—oral, TM *p<0.05, one-way ANOVA, Bonferroni/Dunn post-hoc analysis.

Sublingual Vaccination Performs in a Manner Similar to that of Traditional Intramuscular Vaccination with Respect to Survival After Exposure to Mouse-Adapted Ebola Zaire.

To compare the efficacy of sublingual vaccination to that of traditional intramuscular injection, mice were divided into 6 groups, vaccinated as discussed in more detail below and then the subsequent survival rate (FIG. 13A) and change in body weight (FIG. 13B) were recorded.

Figure 13A:
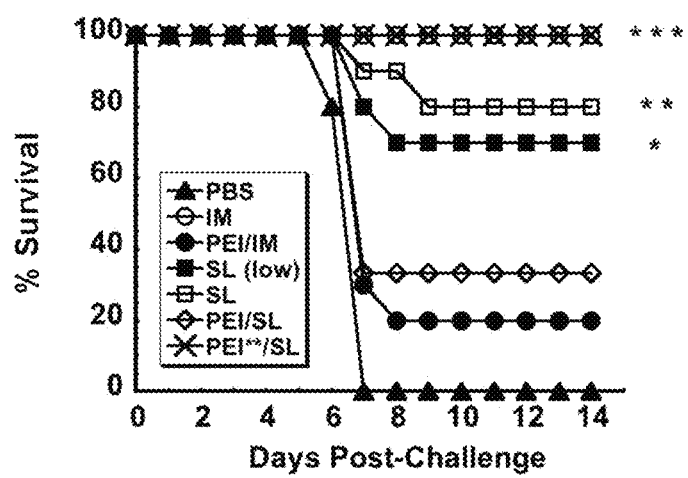
FIG. 13A is a graph depicting the survival rate of six different groups of mice which have been exposed to mouse-adapted Ebola Zaire.
Figure 13B:
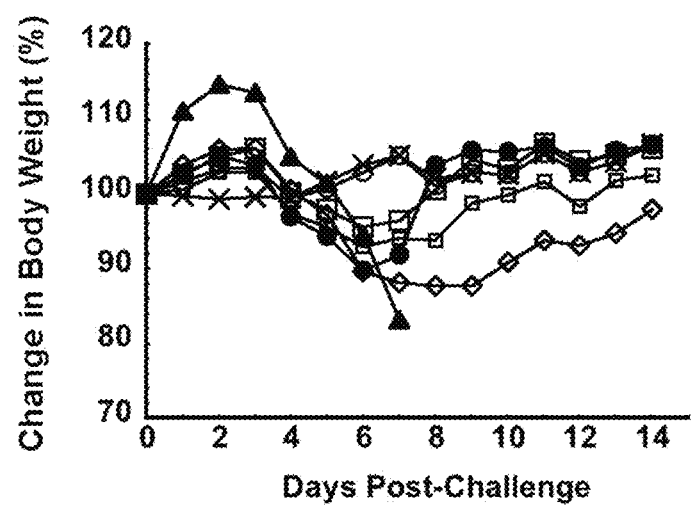
FIG. 13B is a graph depicting the change of body weight for six different groups of mice which have been exposed to mouse-adapted Ebola Zaire.
Figures 14A, 14B, 14C, 14D, 14E:
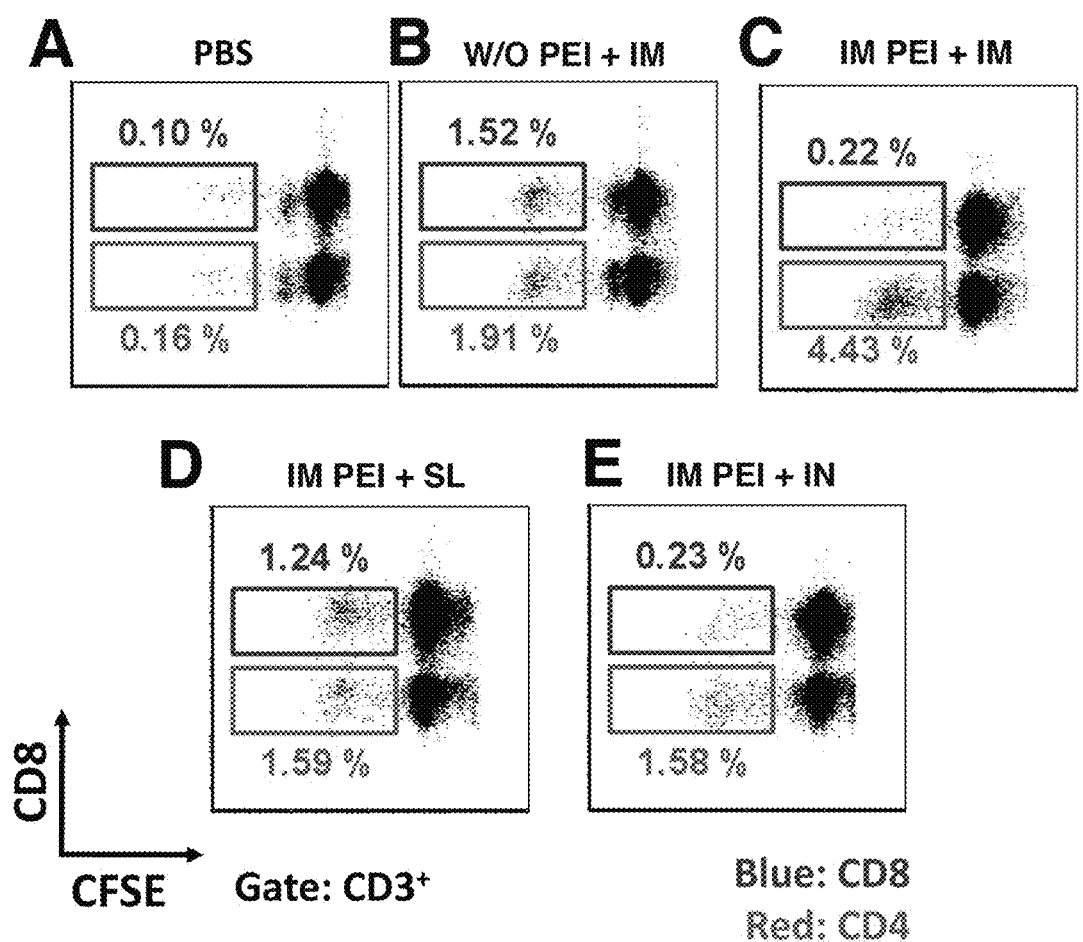
FIGS. 14A-14E depict data obtained in naïve mice 10 days after intramuscular immunization. This data shows that there is an even distribution of CD8+ and CD4+ T cells activated against the adenovirus.

As shown in FIG. 13A, the first group consisted of control animals that were given phosphate buffered saline ("PBS") (not vaccinated). These animals expired within 7 days after exposure to mouse-adapted Ebola Zaire.

The second group contained animals that were vaccinated by intramuscular injection ("IM"). None of the animals expired after exposure to mouse-adapted Ebola Zaire.

The third group contained animals that were pre-exposed to adenovirus (the carrier for the vaccine) 28 days prior to vaccination via intramuscular injection ("IM PET/IM") at a dose of $2.5 \times 10^{11}$ particles or 5 times that used in standard evaluations of pre-existing immunity to adenovirus in the mouse.

The fourth group contained animals that were vaccinated via the sublingual mucosa with a low dose of vaccine ($1 \times 10^7$ infectious virus particles) ("SL (low)"). Note this is one log lower than what was given by the intramuscular route ($1 \times 10^8$ infectious particles). 30% of the animals expired after exposure to mouse-adapted Ebola Zaire.

The fifth group contained animals that were vaccinated via the sublingual mucosa with the same dose of vaccine that was given by the intramuscular route ($1 \times 10^8$ infectious particles) ("SL"). 20% of the animals expired after exposure to mouse-adapted Ebola Zaire.

The sixth group contained animals that were exposed to adenovirus (the carrier for the vaccine) 28 days prior to vaccination via the sublingual mucosa ("IM PEI/SL") at a dose of $2.5 \times 10^{11}$ particles.

The seventh group contained animals that were exposed to adenovirus (the carrier for the vaccine) for 28 days prior to vaccination via the sublingual mucosa (PEI**/SL) at a dose of $5 \times 10^{10}$ virus particles, the standard dose used in evaluations of pre-existing immunity to adenovirus in the mouse. Pre-exposure at this dose did not compromise vaccine efficacy and 100% of the animals survived challenge after exposure to mouse-adapted Ebola Zaire.

It is important to note that the mice were given a dose of Ebola that is considered toxic to primates—approximately 150 times more virus than was necessary. Given this information, it is believed that vaccination via sublingual administration is as effective as a single dose of vaccine given by intramuscular injection.

Sublingual Vaccination Does Not Promote Preferential Production of Anti-Adenovirus CD4+ Memory T Cells in Mice with Prior Exposure to Adenovirus. A significant problem with the use of adenovirus-based vaccines in those with prior exposure to adenovirus is that the innate response to the virus carrier facilitates and favors the production of anti-adenovirus CD4+ memory T cells. While this can compromise the efficiency of subsequent booster immunizations if they are warranted, this is significant in the context of certain disease states. In a recent trial using an adenovirus-based vaccine against HIV it was found that patients with prior exposure to adenovirus actually had a higher chance of obtaining HIV than people that did not have prior contact with the virus. Further investigation revealed this favoring of CD4 T cell expansion, a primary site for HIV infection and replication, in response to the adenovirus was providing an optimal setting for AIDS to develop. For additional information see Benlahrech A, et al., "Adenovirus vector vaccination induces expansion of memory CD4 T cells with a mucosal homing phenotype that are readily susceptible to HIV-1." *Proc. Natl. Acad. Sci. U.S.A.* 2009 Nov. 24; 106(47):19940-19945.

FIGS. 14A-14E show data obtained in naïve mice 10 days after intramuscular immunization. This data reveals that there is an even distribution of CD8+ (1.52%, upper box, blue text, FIG. 14B) and CD4+ T cells (1.91%, lower box, red text, FIG. 14B) activated against the adenovirus. In mice with prior exposure to adenovirus, intramuscular immunization does favor production of CD4+ T cells (4.43% vs. 0.22% CD8+). A similar trend was noted for intranasal immunization. Sublingual immunization of mice with pre-existing immunity to the virus, however, produces an even amount of CD4+ and CD8+ T cells, similar to what is seen in naïve animals (1.24% CD8 vs. 1.59% CD4). This strongly suggests that sublingual administration of adenovirus-based vaccines may be useful in those with HIV.

EXAMPLE 2

An antigen was dispersed within an amorphous solid in the following manner. A stock solution sucrose (400 mg/ml), sorbitol (400 mg/ml) and poly(ethylene) glycol 3000 (10%) was directly mixed with antigen (adenovirus $5 \times 10^{12}$ particles to create a final formulation of sucrose (400 mg/ml), sorbitol (400 mg/ml) and poly(ethylene) glycol 3000 (10%) at a concentration known to induce the desired immune response. The solution was stirred at ambient temperature under aseptic conditions on a magnetic stir plate until the mixture appeared homogeneous. The mixture was then placed briefly in a cooled sonicating waterbath at medium intensity to remove any air bubbles that may have developed in the formulation during its preparation. The final formulation was then dispensed onto a flat backing surface in a laminar flow hood and allowed to dry at ambient temperatures (15-20° C.).

Figure 1:
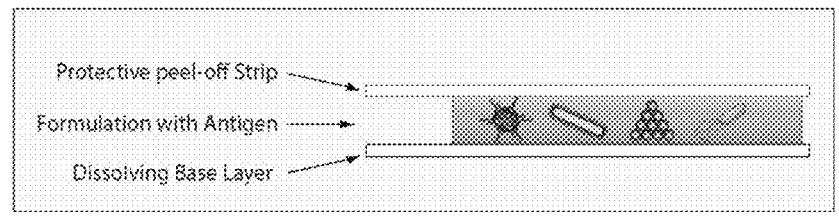
FIG. 1 is an illustration of a vaccine composition of the present disclosure, according to one embodiment.
Figure 2:
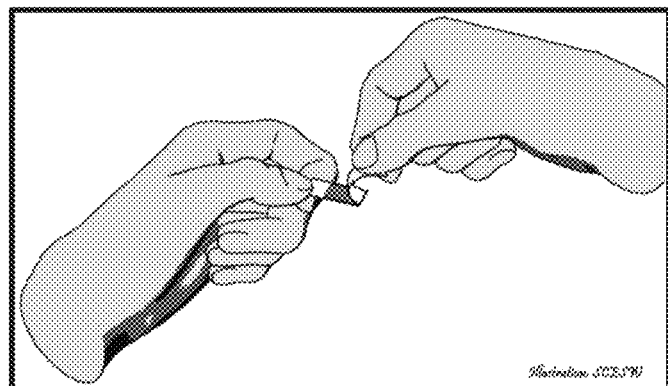
FIG. 2 is an illustration of the removal of a layer of film prior to vaccine administration, according to one embodiment.
Figure 3:
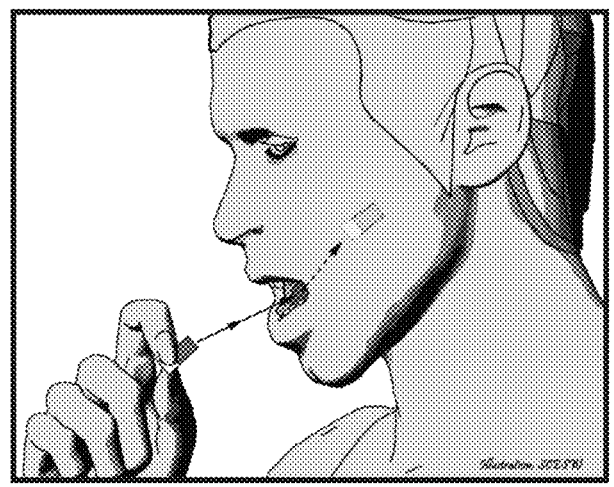
FIG. 3 is an illustration depicting buccal administration of a vaccine composition of the present disclosure, according to one embodiment.
Figures 4A, 4B, 4C, 4D:
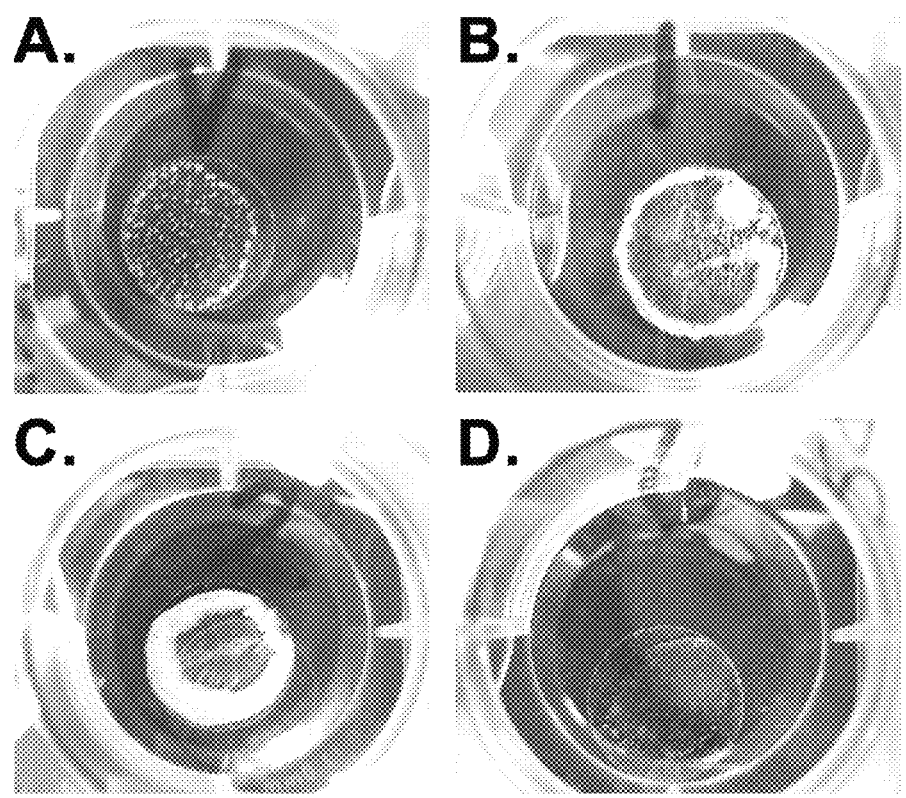
FIGS. 4A-4D depict representative images of dried formulations of a virus-based vaccine for buccal administration after storage at room temperature (25° C.) for one month.
Figure 5:
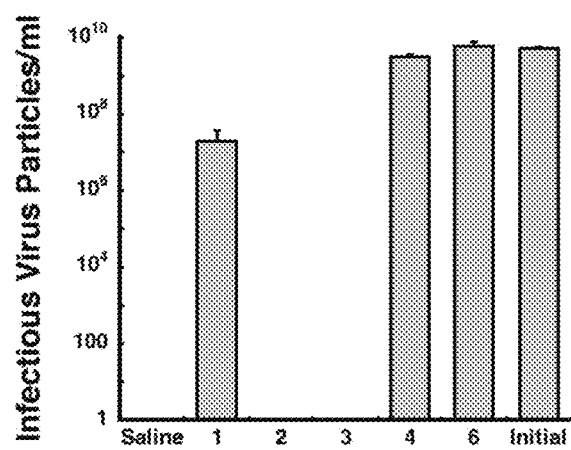
FIG. 5 is a graph depicting the ability of various formulations to preserve virus infectivity after dry storage for one month.
Figures 15A, 15B, 15C, 15D:
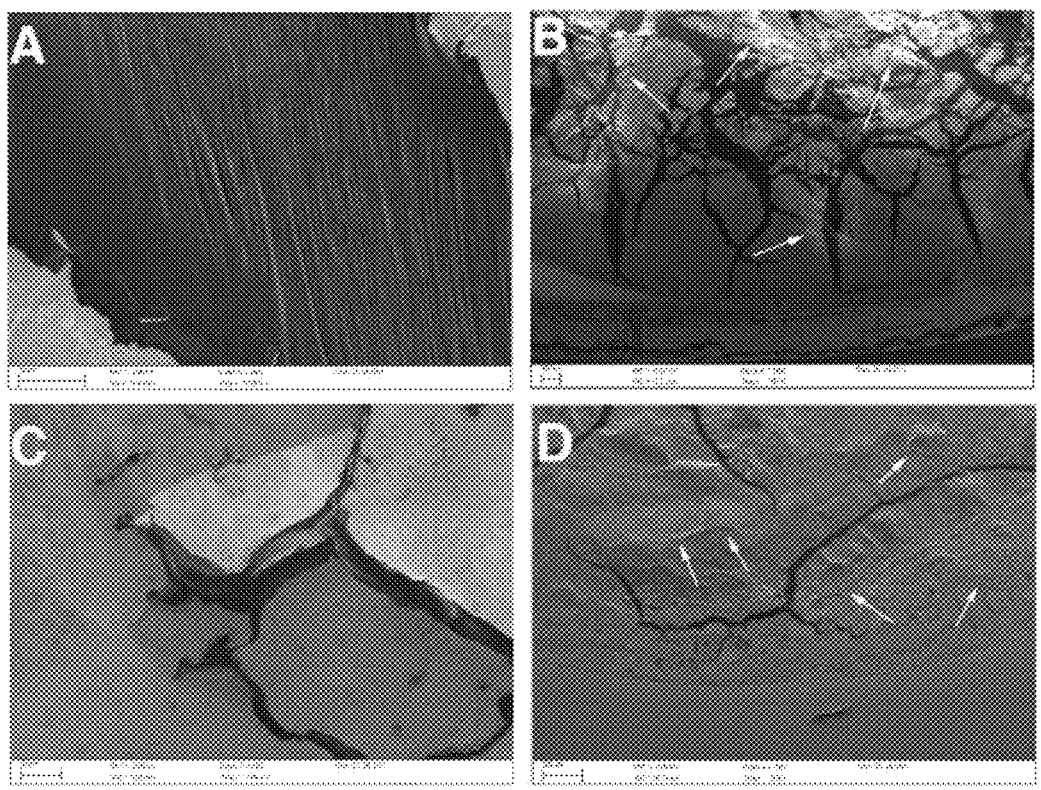
FIGS. 15A-15D depict scanning electron micrographs of dried films containing a recombinant adenovirus-based vaccine.

The physical properties of the antigen, certain concentrations and combinations of sugars and sugar derivates and the backing material prevent rigid alignment of water molecules in the dry state and instead foster the formation of an amorphous solid and pockets of antigen that are evenly dispersed throughout. Examples of these pockets as visualized in a final project by scanning electron microscopy are illustrated in FIG. 15D. There is no flowing liquid trapped in these pockets, instead antigens are suspended in an amorphous solid in their native three dimensional state that is not compromised upon rehydration as illustrated by the infectious titer data in FIG. 5.

FIG. 15A depicts a compartive electron micrograph of an outer surface of a film containing sucrose (10 mg/ml), sorbitol (40 mg/ml) and 0.001% Pluronic F68. Long spiky crystals are notably obvious throughout the formulation after the drying process is complete. FIG. 15B is a cross section of a dried film. The arrows indicate patches of crystal growth present throughout the film. FIG. 15C is an electron micrograph of outer surface of an amorphous solid containing sucrose (40 mg/ml), sorbitol (40 mg/ml) and poly(ethylene) glycol 3000 (1%). This surface is notably smoother than that illustrated in FIG. 15A without notable crystal formation observed even when the film is broken (dark edges in photo). FIG. 15D is a cross section of dried film. The arrows illustrate pockets within the amorphous solid where antigen collects. The large cracks in films depicted in FIG. 15B and FIG. 15D are artifacts created from peeling films from backing material.

EXAMPLE 3

Effect of Pre-Existing Immunity (PEI) to the Vaccine Carrier on Zaire Ebola Glycoprotein-Specific Multifunctional CD8+ T Cell Responses After Sublingual Immunization Naïve B10.Br mice and those with PEI established by the intramuscular (IM) or intranasal (IN) routes (10/group) were given $1 \times 10^8$ infectious virus particles (ivp) of a Ad-CAG-optZGP sublingually. Ad-CAGoptZGP is a replication incompetent adenovirus serotype 5 vector that contains an optimized coding sequence for the Ebola Zaire glycoprotein. FIG. 16A shows analysis of CD8+ T cells expressing immunoreactive cytokines by flow cytometery (FACS). Numbers written in the upper right corner of each scatter plot represent the portion of each cell population that was activated by Ebola Zaire GP-specific peptide sequences. FIG. 16B depicts cumulate analysis of FACS data. Each positively responding cell is assigned to total 7 possible combinations of IFN-γ, IL-2 and TNF-α and final numbers presented as a bar graph. FIG. 16C is a depiction of Zaire GP-specific multifunctional $CD8^+$ T cells in pie chart format. Triple producers (cells producing IFN-γ, IL-2 and TNF-α) are depicted in the red arc. The blue arc highlights cells producing IFN-γ only. Numbers in the pie chart denote the percentage of triple producers in a given population. Results are reported as the mean±the standard error of the mean. **p<0.01, one-way ANOVA, Bonferroni/Dunn post-hoc analysis.

To further characterize the impact of PEI induction by the systemic or mucosal route on vaccine induced $CD8^+$ T cell responses, a more comprehensive functional analysis of cytokine producing $CD8^+$ T cells using multi-parameter flow cytometry was performed. With this strategy, seven distinct cytokine-producing cell populations were delineated and characterized at the single-cell level based on varying combinations of IFN-γ, IL-2 and TNF-α secretion patterns. The relative frequency of these distinct populations defines the quality of the vaccine-induced $CD8^+$ response. Complete analysis of IFN-γ producing cells identified four distinct cell populations: those that produced only IFN-γ, those that produced IFN-γ and IL-2, those that produced IFN-γ and TNF-α and those that produced IFN-γ, IL-2, and TNF-α at the same time. This analysis further revealed a correlation between the frequency of multifunctional $CD8^+$ T cells (those that produced all three cytokines in response to the Ebola glycoprotein antigen) and the manner by which PEI was induced in mice immunized by SL route. As shown in FIG. 16A, the total frequency of IFN-γ producing $CD8^+$ T cells was reduced by prior exposure to the adenovirus vaccine carrier induced by intramuscular injection (0.66%: IM PEI/SL) and by instillation in the respiratory tract (0.21%: IN PEI/SL) with respect to naïve mice that had not been exposed to adenovirus prior to immunization (Naïve, 1.91%). Despite this, a significant rise in the quality of the response was noted when pre-existing immunity was induced by the IM route (24.20±0.91%: Naive/SL vs. 37.04±1.91%: IM PEI/SL, p<0.01; FIG. 16C). The quality response was also not compromised by when PEI was induced by the respiratory route in this treatment group (24.20±0.91%: Naive/SL vs. 20.93±4.92%: IN PEI/SL, p>0.05; FIG. 16C).

EXAMPLE 4

Figure 17A:
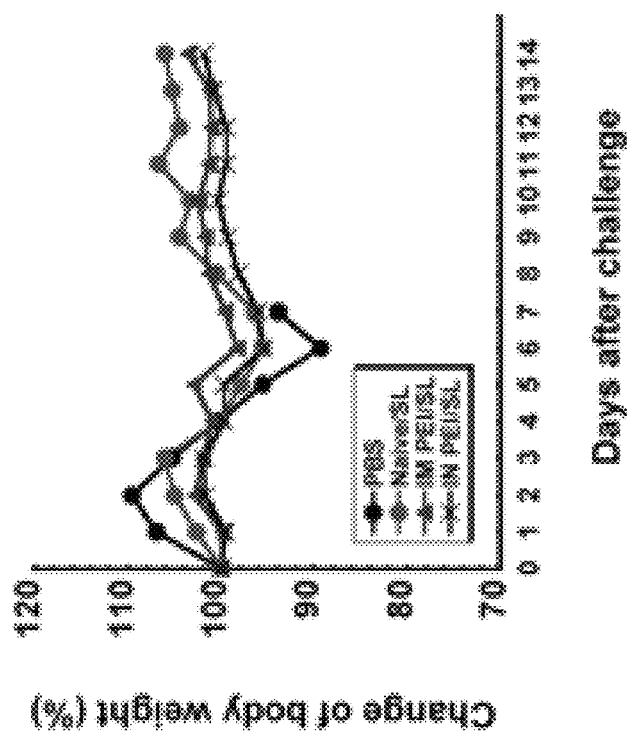
Figure 17B:
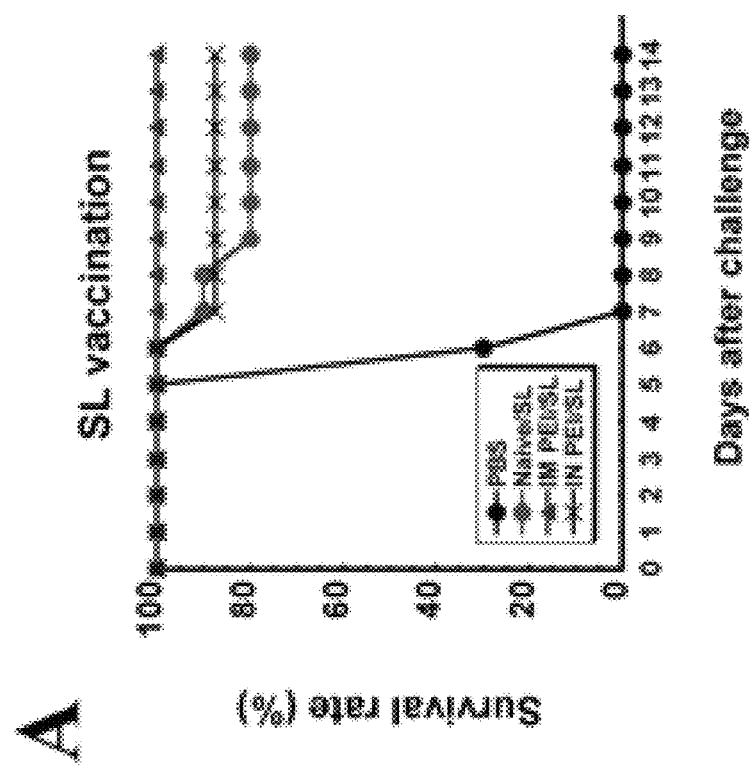
Figure 17C:
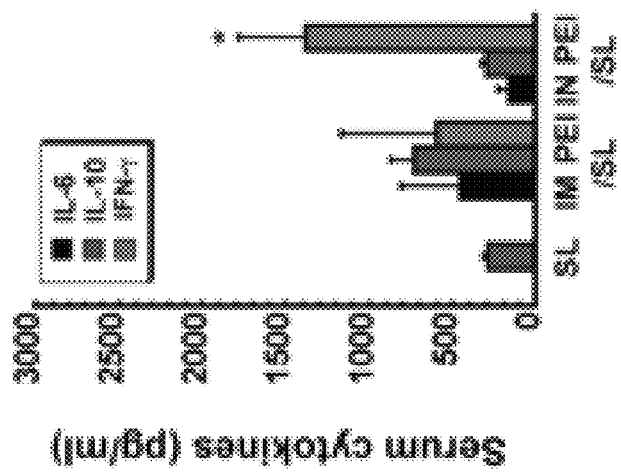
Figure 17D:
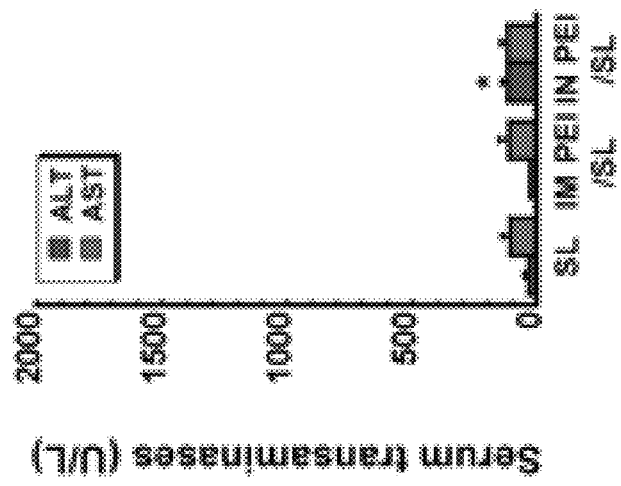

Pre-Existing Immunity to the Adenovirus Carrier Improves Survival After Sublingual Immunization To fully define how PEI affects the immune response generated by sublingual immunization, naïve mice and those with systemic or mucosal PEI were challenged with a lethal dose of mouse-adapted Ebola Zaire (1,000 pfu≃30,000× $LD_{50}$) 28 days after sublingual immunization. Survival, weight loss and toxicity were closely monitored. The challenge was uniformly lethal in control mice given saline (PBS, FIG. 17A). Eighty percent of naïve mice survived without notable loss of body weight (FIG. 17A, B). Interestingly, PEI induced by the respiratory route did not significantly compromise the efficacy of the vaccine with 87.5% survival observed in this treatment group (IN PEI/SL, FIG. 17A). More strikingly, complete (100%) survival was noted in animals with pre-existing immunity induced by the respiratory route, indicating that PEI boosts the potency of the vaccine. This is an exciting finding since prior exposure to adenovirus in the general population primarily occurs through the respiratory mucosa and that, in the United States alone, approximately 30-60% of the population has high levels of anti-adenovirus antibodies while 40-80% of those in Europe and Asia contain similar levels of neutralizing antibody (NAB). The highest levels recorded to date are found in sub-Saharan Africa (80-100% positive). Serum transaminases of naïve mice and those with PEI induced by the IM route were not significantly elevated during challenge (ALT, Naive/SL: 39±14.39 U/L, IM PEI/SL: 31.75±2.89 U/L; p>0.05) and (AST, Naive/SL: 108.5±32.15 U/L, IM PEI/SL: 114±38.42 U/L; p>0.05). This indicates that SL immunization in naïve animals and those with IM PEI prevented hepatotoxicity associated with Zaire Ebola infection (FIG. 17C).

EXAMPLE 5

Effect of PEI on Survival After Lethal Challenge in Guinea Pigs

The protective efficacy of SL immunization in guinea pigs in the presence of systemic or mucosal PEI was evaluated. Guinea pigs (n=5/group) were challenged with 1,000×$LD_{50}$ of guinea pig-adapted ZEBOV (GP-ZEBOV) by i.p. injection. Disease progression was followed and signs and symptoms of infection measured as described for mice. Untreated guinea pigs (negative control: PBS) demonstrated significant weight loss starting from day 5 post-challenge that progressed until death on days 6 to 9 (FIGS. 18A, B). Consistent with the mouse challenge results, 80% of naïve mice and those with systemic PEI vaccinated by the SL route (Naïve/SL, IM PEI/SL) survived without notable loss of body weight (FIG. 18A, B). However, mucosal PEI did significantly compromise the efficacy of the vaccine when given by the SL route with only 40% survival observed in this treatment group (IN PEI/SL, p<0.05, FIG. 18A). Samples taken from guinea pigs post-challenge did not contain significantly elevated serum transaminases (ALT, Naive/SL: 46±2.16 U/L, IM PEI/SL: 40±5.63 U/L, IN PEI/SL: 34.33±7.80 U/L) and (AST, Naive/SL: 65±10.6 U/L, IM PEI/SL: 201.5±120.5 U/L, IN PEI/SL: 218±173.2 U/L) levels after challenge (FIG. 18C).

EXAMPLE 5

Effect of Formulation #16 on the In Vivo Performance of our Ebola Vaccine

Formulation 16 is a formulation comprising the amphipathic surfactant, poly (Maleic Anhydride-Alt-1 Octadecene substituted with 3-(dimethylamino) propylamine (PMAL-C16) at a concentration of 10 mg/ml in phosphate buffered saline (pH 7.4). The vaccine was directly placed in this solution prior to administration to animals.

Figure 19A:
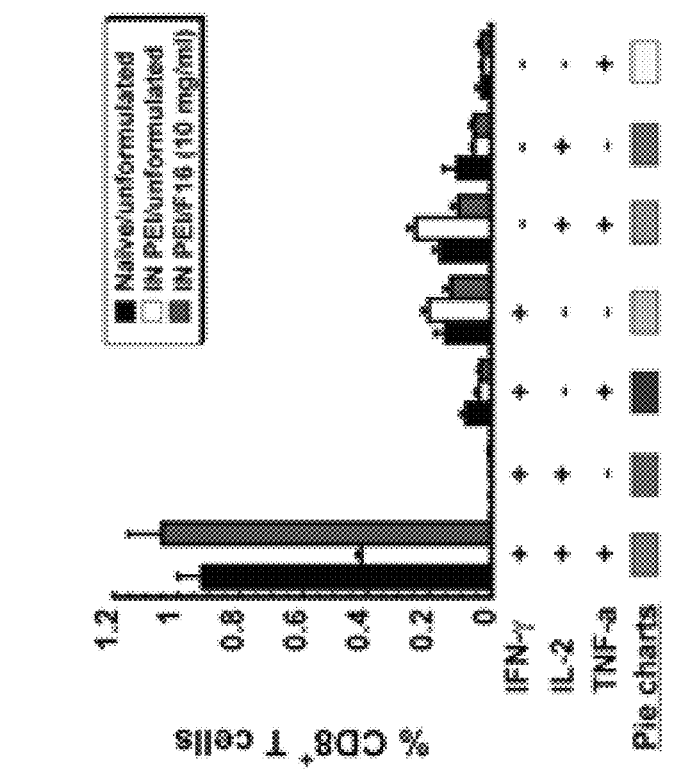
Figure 19B:
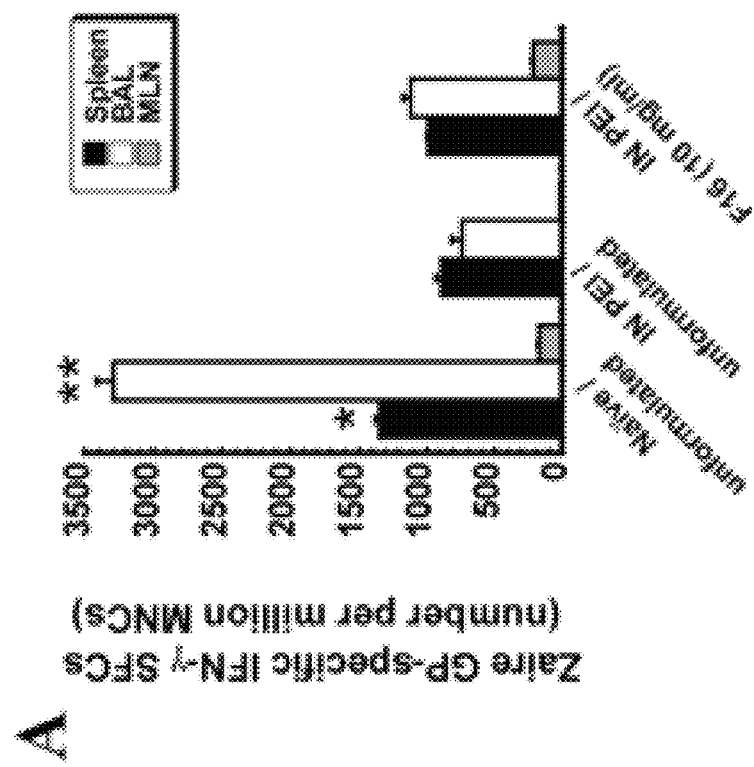
Figures 19C, 19D:
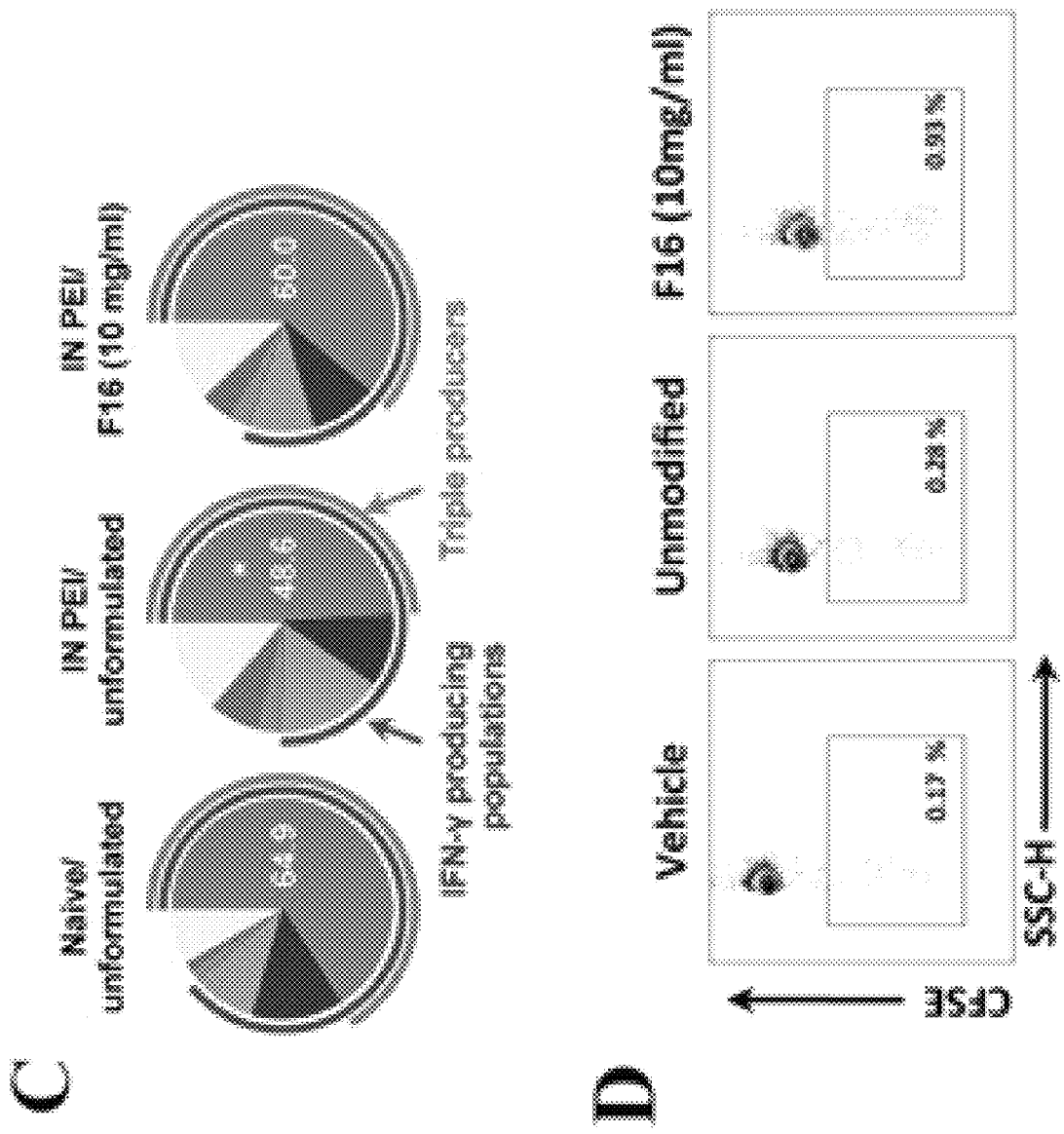

Mucosal PEI significantly compromised the production of Zaire GP-specific IFN-γ-secreting mononuclear cells isolated from spleen and other mucosal compartments (BAL, MNLs) in mice given either unformulated or formulated vaccine (FIG. 19A). As expected, mucosal PEI did significantly reduce the frequency of Zaire GP-specific multifunctional $CD8^+$ T cells elicited by the unformulated vaccine (Naïve: 64.9±4.88% vs. IN PEI: 48.6±3.66%, p<0.05; FIG. 19C). Although PEI did reduce the magnitude of IFN-γ$^+$ secreting cells in mice given the F#16 preparation, the multifunctional $CD8^+$ T cell responses did not change (Naïve/unformulated: 64.9±4.88% vs. IN PEI/F16 (10 mg/ml): 60.0±9.1%, p>0.05; FIG. 19C). The memory response evaluated in mice given either unformulated or formulated vaccine revealed that formulation #16 increased the memory response by a factor of 3.3 from 0.28±0.15% (unmodified) to 0.93±0.25% (formulation #16), (FIG. 19D).

EXAMPLE 6

Figure 20A:
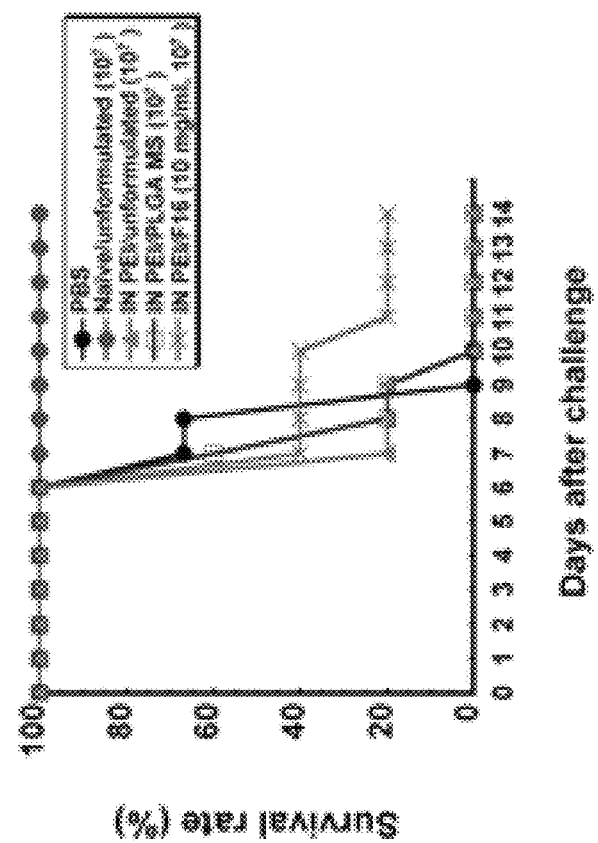
Figure 20B:
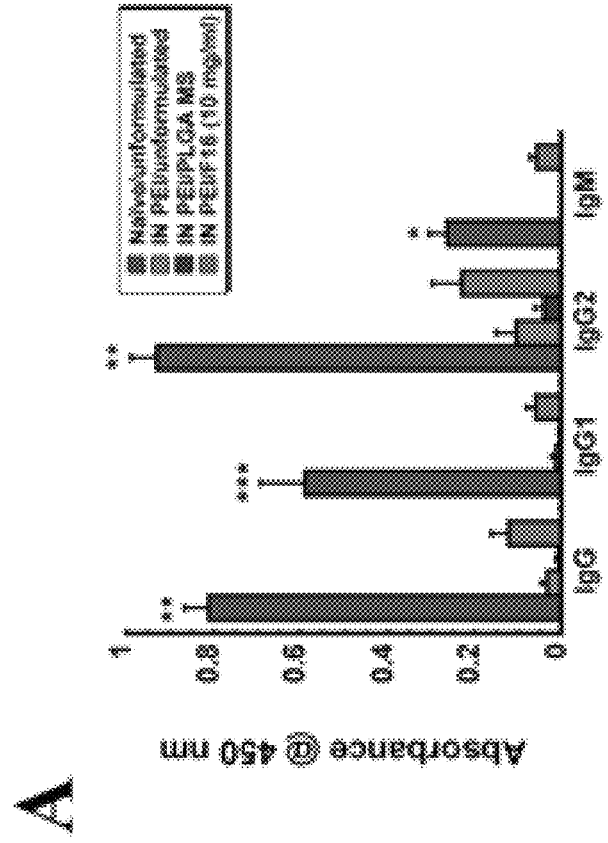
Figure 20C:
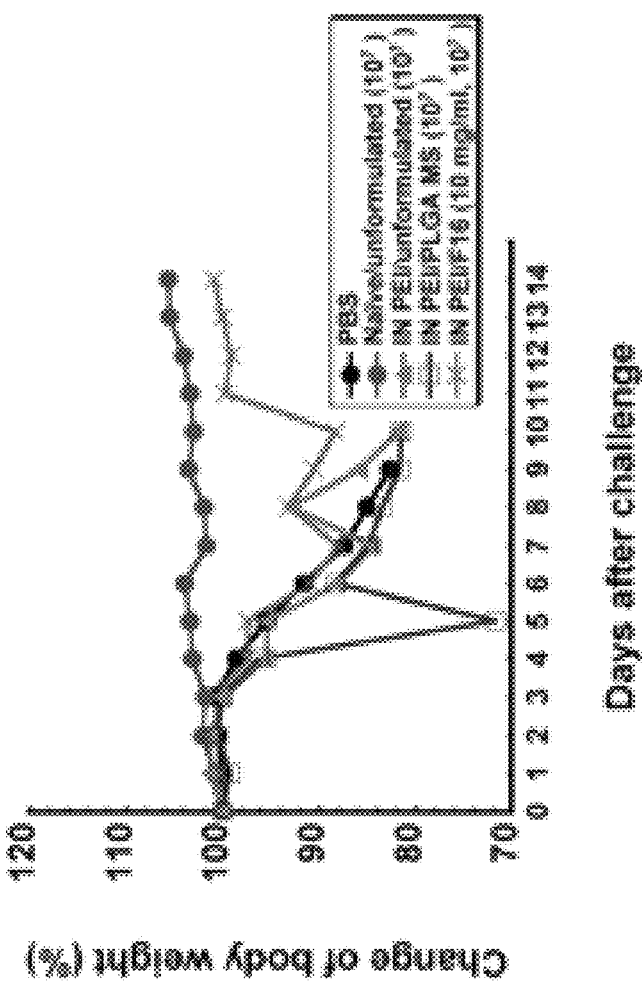
Figure 20D:
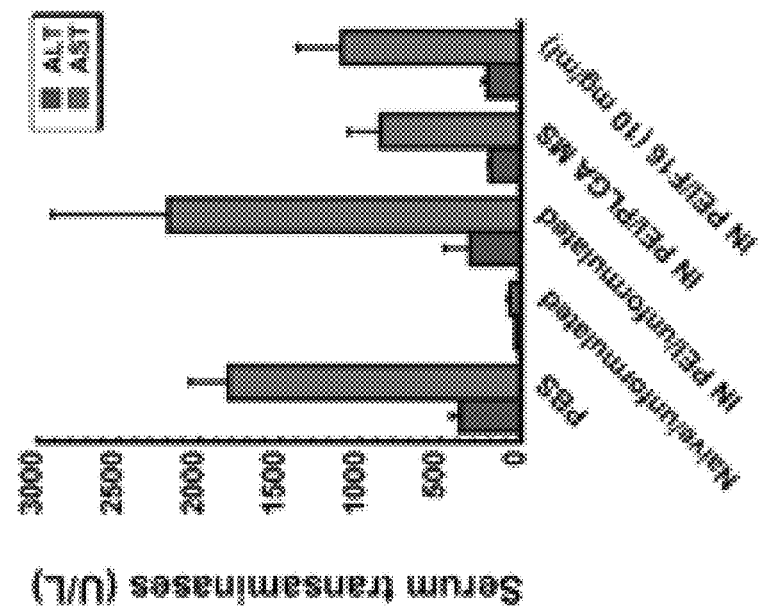

Effect of Formulation #16 (F16) on Survival After Lethal Challenge in Guinea Pigs Since disease progression and pathogenesis of Ebola infection in guinea pigs more closely resembles those of the human disease than what is seen in the mouse, the protective efficacy of the vaccine formulated with F16 was tested directly in this animal model with a 10-fold lower dose than what was used in the previous challenge studies (1×10$^7$ ivp/guinea pig). Prior to challenge, serum Zaire Ebola glycoprotein-specific immunoglobulin isotype levels were evaluated to characterize the effect of the formulation on B cell-mediated antibody responses in this animal model. PEI significantly compromised anti-Zaire GP-specific IgG isotypes and IgM in levels with respect to the levels attained in naïve animals given unformulated vaccine. Total IgG, IgG1, IgG2 and IgM were reduced by 95.8%, 97.8%, 88.7% and 99.4%, respectively, compared to the vaccine given to naïve guinea pigs (FIG. 20A). Formulation #16 increased the antigen-specific antibody responses with respect to the vaccine embedded in a poly(lactic)-co-glycolic acid (PLGA) biodegradable polymer which had previously been shown to increase survival in animals with prior exposure to adenovirus. Thus, F16 increased total IgG, IgG1, IgG2 and IgM were increased by 12.6%, 8.9%, 16.7% and 21.1%, respectively (FIG. 20A). The protective efficacy of formulation #16 in guinea pigs with mucosal PEI was also evaluated. Complete protection was achieved in naïve guinea pigs given unformulated vaccine without notable loss of body weight (FIG. 20B, C). Mucosal PEI did significantly compromise the efficacy of the unformulated vaccine when given by the same route as there were no survivors in this treatment group (IN PEI/unformulated, FIG. 20B). PLGA encapsulated vaccine had no beneficial effect on survival at a low immunization dose but, formulation #16 did increase the survival from 0% (IN PEI/unformulated or PLGA) to 20% (FIG. 20B). Samples taken from guinea pigs with PEI post-challenge did contain elevated serum AST (IN PEI/ unformulated: 2192±726.3 U/L, IN PEI/PLGA MS: 879±197 U/L, IN PEI/F16: 1119±277.9 U/L) with respect to naïve animals (74.4.75±13.78 U/L), indicative of severe liver damage from Zaire Ebola infection (FIG. 20D).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. Abbink, P., Lemckert, A. A., Ewald, B. A., Lynch, D. M., Denholtz, M., Smits, S., Holterman, L., Damen, I., Vogels, R., Thorner, A. R., O'Brien, K. L., Carville, A., Mansfield, K. G., Goudsmit, J., Havenga, M. J., and Barouch, D. H. (2007). Comparative seroprevalence and immunogenicity of six rare serotype recombinant adenovirus vaccine vectors from subgroups B and D. *J. Virol.* 81(9): 4654-4663.
2. AVMA Guidelines on Euthanasia (Formerly Report of the AVMA Panel on Euthanasia) June 2007. (avma.org/resources/euthanasia.pdf)
3. Bae, K., Choi, J., Jang, Y., Ahn, S., and Hur, B. (2009). Innovative vaccine production technologies: the evolution and value of vaccine production technologies. *Arch. Pharm. Res.* 32(4): 465-480.
4. Beilin, B., Martin, F. C., Shavit, Y., Gale, R. P., and Liebeskind, J. C. (1989). Suppression of natural killer cell activity by high-dose narcotic anesthesia in rats. Brain Behav Immun. 3, 129-137.
5. Bolton, D. L., and Roederer, M. (2009). Flow cytometry and the future of vaccine development. *Expert Rev. Vaccines.* 8(6): 779-789.
6. Bolton, S. (1997). Pharmaceutical Statistics Practical and Clinical Applications. New York, N.Y., Marcel Dekker, Inc.
7. Bray, M., Davis, K., Geisbert, T., Schmaljohn, C., and Huggins, J. (1998). A mouse model for evaluation of prophylaxis and therapy of Ebola hemorrhagic fever. J Infect Dis. 178, 651-661.
8. Bray, M., Hatfill, S., Hensley, L., and Huggins, J. W. (2001). Haematological, biochemical and coagulation changes in mice, guinea-pigs and monkeys infected with a mouse-adapted variant of Ebola Zaire virus. J. Comp. Pathol. 125, 243-253.
9. Chen, D., and Kristensen, D. (2009). Opportunities and challenges of developing thermostable vaccines. *Expert Rev. Vaccines.* 8(5): 547-557.
10. Connolly, B. M., Steele, K. E., Davis, K. J., Geisbert, T. W., Kell, W. M., Jaax, N. K., and Jahrling, P. B. (1999). Pathogenesis of experimental Ebola virus infection in guinea pigs. J. Infect. Dis. 1999 February; 179 Suppl 1:S203-17. 179, S203-S207.
11. Costantino, H. R., Illum, L., Brandt, G., Johnson, P. H., and Quay, S. C. (2007). Intranasal delivery: physicochemical and therapeutic aspects. *Int. J. Pharm.* 337(1-2): 1-24.
12. Croyle, M. A., Patel, A., Tran, K. N., Gray, M., Zhang, Y., Strong, J. E., Feldmann, H., and Kobinger, G. P. (2008). Nasal delivery of an adenovirus-based vaccine bypasses pre-existing immunity to the vaccine carrier and improves the immune response in mice. *PLoS One* 3(10): e3548.
13. Desvignes, C., Esteves, F., Etchart, N., Bella, C., Czerkinsky, C., and Kaiserlian, D. (1998). The murine buccal mucosa is an inductive site for priming class I-restricted CD8+ effector T cells in vivo. *Clin. Exp. Immunol.* 113(3): 386-393.
14. Ducusin, J., Narvaez, D., Wilburn, S., Mahmoudi, F., Orris, P., Sobel, H., Bersola, E., and Ricardo, M. (2004). Waste Management and Disposal During the Philippine Follow-Up Measles Campaign. Washington, D.C., U.S.A. and Manila, Phillipines, Health Care without Harm and the Philippine Department of Health: 1-112.
15. Geisbert, T. W., Pushko, P., Anderson, K., Smith, J., Davis, K. J., and Jahrling, P. B. (2002). Evaluation in nonhuman primates of vaccines against Ebola virus. Emerg Infect Dis 8, 503-507.
16. Geber, W. F., Lefkowitz, S. S., and Hung, C. Y. (1977). Duration of interferon inhibition following single and multiple injections of morphine. J. Toxicol. Environ. Health. 2, 577-582.
17. Giudice, E. L., and Campbell, J. D. (2006). Needle-free vaccine delivery. *Adv. Drug Deliv. Rev.* 58(1): 68-89.
18. Hassan, N., Ahad, A., Ali, M., and Ali, J. (2010). Chemical permeation enhancers for transbuccal drug delivery. *Expert Opin Drug Deliv.* 7(1): 97-112.
19. Hill, M. W. (1984). Cell Renewal in Oral Epithelia. The Structure and Function of Oral Mucosa. J. Meyer, Squier, C. A., Gerson, S. J., Eds. New York, Pergamon.
20. Hutton, G., and Tediosi, F. (2006). The costs of introducing a malaria vaccine through the expanded program on immunization in Tanzania. *Am. J. Trop. Med. Hyg.* 75(2 Suppl.): 119-130.
21. Hung, C. Y., Lefkowitz, S. S, and Geber, W. F. (1973). Interferon inhibition by narcotic analgesics. Proc. Soc. Exp. Biol. Med. 142, 106-111.

22. Ibrahim, J., Gerson, S. J., and Meyer, J. (1985). Frequency and distribution of binucleate cells in oral epithelium of several species of laboratory rodents. *Arch. Oral Biol.* 30(8): 627-633.
23. Ingulli, E. (2007). Tracing tolerance and immunity in vivo by CFSE-labeling of administered cells. *Methods Mol. Biol.* 380: 365-376.
24. Jacobsen, J., Nielsen, E. B., Brøndum-Nielsen, K., Christensen, M. E., Olin, H. B., Tommerup, N., Rassing, M. R. (1999). Filter-grown TR146 cells as an in vitro model of human buccal epithelial permeability. *Eur. J. Oral Sci.* 107(2): 138-146.
25. Jacobson, R. M., Swan, A., Adegbenro, A., Ludington, S. L., Wollan, P. C., and Poland, G. A. (2001). Making vaccines more acceptable—methods to prevent and minimize pain and other common adverse events associated with vaccines. *Vaccine* 19(17-19): 2418-2427.
26. Kane, A., Lloyd, J., Zaffran, M., Simonsen, L., and Kane, M. (1999). Transmission of hepatitis B, hepatitis C and human immunodeficiency viruses through unsafe injections in the developing world: model-based regional estimates. *Bull. World Health Organ.* 77(10): 801-807.
27. Kobinger, G. P., Feldmann, H., Zhi, Y., Schumer, G., Gao, G., Feldmann, F., Jones, S., and Wilson, J. M. (2006). Chimpanzee adenovirus vaccine protects against Zaire Ebola virus. *Virology* 346(2): 394-401.
28. Levine, M. M., and Robins-Browne, R. (2009). Vaccines, global health and social equity. *Immunol. Cell Biol.* 87(4): 274-278.
29. Mao, S., Cun, D., and Kawaashima, Y. (2009). Novel Non-Injectable Formulation Approaches of Peptides and Proteins. Delivery Technologies for Biopharmaceuticals Peptides, Proteins, Nucelic Acids and Vaccines. L. Jorgensen, and Nielsen, H. M., Eds. West Sussex, United Kingdom, John Wiley & Sons Ltd.: 29-67.
30. Marone, G., Stellato, C., Mastronardi, P., Mazzarella, B. (1993). Mechanisms of activation of human mast cells and basophils by general anesthetic drugs. Ann. Fr. Anesth. Reanim. 12, 116-125.
31. Matthias, D. M., Robertson, J., Garrison, M. M., Newland, S., and Nelson, C. (2007). Freezing temperatures in the vaccine cold chain: a systematic literature review. *Vaccine* 25(20): 3980-3986.
32. Mutsch, M., Zhou, W., Rhodes, P., Bopp, M., Chen, R. T., Linder, T., Spyr, C., and Steffen, R. (2004). Use of the inactivated intranasal influenza vaccine and the risk of Bell's palsy in Switzerland. *N. Engl. J. Med.* 350(9): 896-903.
33. Nir, Y., Paz, A., Sabo, E., and Potasman, I. (2003). Fear of injections in young adults: prevalence and associations. *Am. J. Trop. Med. Hyg.* 68(3): 341-344.
34. Nwanegbo, E., Vardas, E., Gao, W., Whittle, H., Sun, H., Rowe, D., Robbins, P. D., and Gambotto, A. (2004). Prevalence of neutralizing antibodies to adenoviral serotypes 5 and 35 in the adult populations of The Gambia, South Africa, and the United States. *Clin. Diagn. Lab Immunol.* 11(2): 351-357.
35. Pather, S. I., Rathbone, M. J., and Senel, S. (2008). Current status and the future of buccal drug delivery systems. *Expert Opin. Drug Deliv.* 5(5): 531-542.
36. Piersma, F. E., Daemen, M. A., Bogaard, A. E., and Buurman, W. A. (1999). Interference of pain control employing opioids in in vivo immunological experiments. Lab Animal 33, 328-333.
37. Prüss-Ustün, A., Rapiti, E., and Hutin, Y. (2005). Estimation of the global burden of disease attributable to contaminated sharps injuries among health-care workers. *Am. J. Ind. Med.* 48(6): 482-490.
38. Reed, L. J., and Muench, H. (1938). A simple method of estimating fifty percent endpoints. *Am. J. Hyg.* 27:493-497.
39. Rupniak, H. T., Rowlatt, C., Lane, E. B., Steele, J. G., Trejdosiewicz, L. K., Laskiewicz, B., Povey, S., Hill, B. T. (1985). Characteristics of four new human cell lines derived from squamous cell carcinomas of the head and neck. *J. Natl. Cancer Inst.* 75(4): 621-635.
40. Russell, K. L., Hawksworth, A. W., Ryan, M. A., Strickler, J., Irvine, M., Hansen, C. J., Gray, G. C., and Gaydos, J. C. (2006). Vaccine-preventable adenoviral respiratory illness in US military recruits, 1999-2004. *Vaccine* 24(15): 2835-2842.
41. Shojaei, A. H. (1998). Buccal Mucosa as a Route for Systemic Drug Delivery: A Review. *J. Pharm. Pharmaceut. Sci.* 1(1): 15-30.
42. Simonsen, L., Kane, A., Lloyd, J., Zaffran, M., and Kane, M. (1999). Unsafe injections in the developing world and transmission of bloodborne pathogens: a review. *Bull. World Health Organ.* 77(10): 789-800.
43. Soma, L. R. (1983). Anesthetic and analgesic considerations in the experimental animal. Ann NY Acad Sci 406, 32-47.
44. Stellato, C., Cirillo, R., de Paulis, A., et al. (1992). Human basophil/mast cell releasability. IX. Heterogeneity of the effects of opioids on mediator release. Anesthesiology. 77, 932-940.
45. Stroher, U., and Feldmann, H. (2006). Progress towards the treatment of Ebola haemorrhagic fever. Expert Opin Investig Drugs 15, 1523-1535.
46. Thacker, E. E., Timares, L., Matthews, Q. L. (2009). Strategies to overcome host immunity to adenovirus vectors in vaccine development. *Expert Rev. Vaccines.* 8(6): 761-777.
47. Wertz, P. W., and Squier, C. A. (1991). Cellular and molecular basis of barrier function in oral epithelium. *Crit. Rev. Ther. Drug Carrier Syst.* 8(3): 237-269.
48. World Health Organization, (2005). Management of solid health-care waste at primary health-care centres : a decision-making guide. Department of Immunization, Vaccines and Biologicals (IVB), Protection of the Human Environment Water, Sanitation and Health (WSH) Immunization, Protection of the Human Environment Water, Sanitation and Health (WSH). Geneva, Switzerland, World Health Organization: 1-53.
49. World Health Organization, UNICEF, and World Bank. (2009). State of the World's Vaccines and Immunization. Geneva, Switzerland, World Health Organization.
50. Yuki, Y., and Kiyono, H. (2009). Mucosal vaccines: novel advances in technology and delivery. *Expert Rev. Vaccines.* 8(8): 1083-1097.

Zhou, W., Pool, V., DeStefano, F., Iskander, J. K., Haber, P., and Chen, R. T. (2004). A potential signal of Bell's palsy after parenteral inactivated influenza vaccines: reports to the Vaccine Adverse Event Reporting System (VAERS)—United States, 1991-2001. *Pharmacoepidemiol. Drug Saf.* 13(8): 505-510.

What is claimed is:

1. A method of generating a vaccine composition, the method comprising:
(a) providing (i) an antigen and (ii) a solution comprising a sugar or sugar derivative and PMAL-C16 (poly (maleic anhydride-alt-1 octadecene) substituted with 3-(dimethylamino) propylamine); and (b) dispersing the antigen within the solution at an ambient temperature.

2. The method of claim 1, further comprising, after dispersing the antigen within the solution, freezing the solution.

3. The method of claim 1, wherein the sugar or sugar derivative is glucose, dextrose, fructose, lactose, maltose, xylose, sucrose, corn sugar syrup, sorbitol, hexitol, maltilol, xylitol, mannitol, melezitose, or raffinose.

4. The method of claim 1, wherein the solution comprises sorbitol.

5. The method of claim 1, wherein, after dispersing the antigen within the solution, the solution comprises 10 mg/ml PMAL-C16.

6. The method of claim 1, wherein the antigen is a virus or portion thereof.

7. The method of claim 6, wherein the virus is present in an amount of from about $1\times10^6$ to about $1\times10^{13}$ virus particles.

8. The method of claim 6, wherein the virus is an adenovirus.

9. The method of claim 1, wherein the antigen is a bacteria or portion thereof.

10. The method of claim 1, wherein the antigen is a peptide.

11. A vaccine composition comprising:
(a) an antigen;
(b) a sugar or sugar derivative of combination thereof; and
(c) PMAL-C16 (poly (maleic anhydride-alt-1 octadecene) substituted with 3-(dimethylamino) propylamine).

12. The vaccine composition of claim 11, wherein the vaccine composition is a liquid.

13. The vaccine composition of claim 12, wherein the vaccine composition comprises 10 mg/ml PMAL-C16.

14. The vaccine composition of claim 11, wherein the sugar or sugar derivative is glucose, dextrose, fructose, lactose, maltose, xylose, sucrose, corn sugar syrup, sorbitol, hexitol, maltilol, xylitol, mannitol, melezitose, or raffinose.

15. The vaccine composition of claim 11, wherein the sugar or sugar derivative is sorbitol.

16. The vaccine composition of claim 11, wherein the antigen is a virus or portion thereof.

17. The vaccine composition of claim 11, wherein the virus is present in an amount of from about $1\times10^6$ to about $1\times10^{13}$ virus particles.

18. The vaccine composition of claim 11, wherein the virus is an adenovirus.

19. The vaccine composition of claim 11, wherein the antigen is a bacteria or portion thereof.

20. The vaccine composition of claim 11, wherein the antigen is a peptide.

* * * * *